(12) United States Patent
Cable et al.

(10) Patent No.: US 7,949,383 B2
(45) Date of Patent: May 24, 2011

(54) IMAGING APPARATUS WITH SELECTABLE MOVEABLE STAGE

(75) Inventors: Michael D. Cable, Danville, CA (US); Michael Bo Nelson, San Francisco, CA (US); Bradley W. Rice, Danville, CA (US); David N Sprague, Fremont, CA (US)

(73) Assignee: Xenogen Corporation, Alameda, CA (US)

( * ) Notice: Subject to any disclaimer, the term of this patent is extended or adjusted under 35 U.S.C. 154(b) by 1762 days.

(21) Appl. No.: 11/139,256

(22) Filed: May 27, 2005

(65) Prior Publication Data
US 2005/0231592 A1  Oct. 20, 2005

Related U.S. Application Data

(62) Division of application No. 10/912,022, filed on Aug. 4, 2004, now Pat. No. 6,901,279, which is a division of application No. 09/795,056, filed on Feb. 21, 2001, now Pat. No. 6,775,567.

(60) Provisional application No. 60/184,859, filed on Feb. 25, 2000.

(51) Int. Cl.
*A61B 5/05* (2006.01)

(52) U.S. Cl. ............................. 600/407; 396/513

(58) Field of Classification Search .................. 600/473, 600/476; 359/398, 391, 393
See application file for complete search history.

(56) References Cited

U.S. PATENT DOCUMENTS

| | | |
|---|---|---|
| 2,854,273 A | 9/1958 | Cunningham |
| 3,566,636 A | 3/1971 | Rudolf et al. |
| 3,655,288 A | 4/1972 | Lieberman et al. |
| 3,871,767 A | 3/1975 | Holm-Hansen et al. |
| 3,969,572 A | 7/1976 | Rostek |
| 4,076,420 A | 2/1978 | De Maeyer et al. |
| 4,332,244 A | 6/1982 | Levy et al. |

(Continued)

FOREIGN PATENT DOCUMENTS
EP  0493707  3/1996

(Continued)

OTHER PUBLICATIONS

Kobayashi M et al. In vivo imaging of spontaneous ultraweak photon emission from a rat's brain correlated with cerebral energy metabolism and oxidative stress. Neuroscience Research 1999;34:103-113.*

(Continued)

*Primary Examiner* — Long V Le
*Assistant Examiner* — Helene Bor
(74) *Attorney, Agent, or Firm* — Beyer Law Group LLP

(57) ABSTRACT

An imaging box assembly is provided for capturing an image of a sample. The imaging box assembly includes a body having an interior cavity for receiving the sample, and having a front portion defining an opening into the cavity. The body further includes a view port enabling viewing of the sample contained in the interior cavity. A door is mounted to the body that is movable between an opened condition, enabling access to the interior cavity through the cavity opening, and a closed condition, positioning a door rear portion substantially adjacent the body front portion to prevent access through the cavity opening. The box assembly further includes a moveable stage disposed in the cavity interior that supports the sample. The moveable stage is adapted to selectively position the sample at a selected one of a plurality of positions relative to the view hole.

16 Claims, 20 Drawing Sheets

U.S. PATENT DOCUMENTS

| | | | |
|---|---|---|---|
| 4,582,406 A | 4/1986 | Wally | |
| 4,593,728 A | 6/1986 | Whitehead et al. | |
| 4,708,475 A | 11/1987 | Watson | |
| 4,828,340 A * | 5/1989 | Jorgensen | 312/7.1 |
| 4,863,690 A | 9/1989 | Berthold et al. | |
| 5,039,868 A | 8/1991 | Kobayashi et al. | |
| 5,064,283 A * | 11/1991 | Tober | 356/73 |
| 5,142,303 A | 8/1992 | Nelson | |
| 5,149,625 A | 9/1992 | Church et al. | |
| 5,157,491 A | 10/1992 | Kassatly | |
| 5,202,091 A | 4/1993 | Lisenbee | |
| 5,216,235 A * | 6/1993 | Lin | 250/201.6 |
| 5,251,021 A | 10/1993 | Parulski et al. | |
| 5,301,006 A | 4/1994 | Bruce | |
| 5,319,209 A | 6/1994 | Miyakawa et al. | |
| 5,414,258 A | 5/1995 | Liang | |
| 5,519,210 A | 5/1996 | Berner | |
| 5,542,012 A | 7/1996 | Fernandes et al. | |
| 5,636,299 A | 6/1997 | Bueno et al. | |
| 5,637,874 A | 6/1997 | Honzawa et al. | |
| 5,650,135 A | 7/1997 | Contag et al. | |
| 5,672,881 A | 9/1997 | Striepeke et al. | |
| 5,680,492 A | 10/1997 | Hopler et al. | |
| 5,705,806 A | 1/1998 | Matsuda et al. | |
| 5,705,807 A | 1/1998 | Throngnumchai | |
| 5,738,101 A | 4/1998 | Sappey | |
| 5,748,236 A | 5/1998 | Shibazaki | |
| 5,840,572 A | 11/1998 | Copeland et al. | |
| 5,843,196 A | 12/1998 | Leavey et al. | |
| 5,867,250 A | 2/1999 | Baron | |
| 5,898,802 A | 4/1999 | Chen et al. | |
| 5,901,849 A | 5/1999 | Blandin et al. | |
| 5,916,160 A | 6/1999 | Arcan et al. | |
| 5,970,164 A | 10/1999 | Bamberger | |
| 5,986,271 A | 11/1999 | Lazarev et al. | |
| 5,992,417 A * | 11/1999 | Toepel | 128/846 |
| 6,022,124 A | 2/2000 | Bourn et al. | |
| 6,036,920 A | 3/2000 | Pantoliano et al. | |
| 6,043,506 A | 3/2000 | Heffelfinger et al. | |
| 6,071,748 A | 6/2000 | Modlin et al. | |
| 6,084,680 A | 7/2000 | Tuunanen et al. | |
| 6,097,025 A | 8/2000 | Modlin et al. | |
| 6,123,437 A | 9/2000 | Holmes | |
| 6,217,847 B1 | 4/2001 | Contag et al. | |
| 6,226,093 B1 | 5/2001 | Lo et al. | |
| 6,242,743 B1 | 6/2001 | DeVito et al. | |
| 6,290,382 B1 | 9/2001 | Bourn et al. | |
| 6,321,111 B1 | 11/2001 | Perelman et al. | |
| 6,364,829 B1 | 4/2002 | Fulghum | |
| 6,381,058 B2 | 4/2002 | Ramm et al. | |
| 6,510,281 B2 | 1/2003 | Schroder | |
| 6,536,430 B1 | 3/2003 | Smith | |
| 6,567,125 B1 | 5/2003 | Shimizu | |
| 6,597,864 B2 | 7/2003 | Schroder | |
| 6,615,063 B1 | 9/2003 | Ntziachristos | |
| 6,625,558 B1 | 9/2003 | Van Ausdall et al. | |
| 6,646,678 B1 * | 11/2003 | Kobayashi | 348/207.1 |
| 6,649,143 B1 | 11/2003 | Contag et al. | |
| 6,775,567 B2 | 8/2004 | Cable et al. | |
| 6,800,452 B1 | 10/2004 | McNeil et al. | |
| 6,867,348 B1 | 3/2005 | Zhang et al. | |
| 6,881,584 B1 | 4/2005 | Lenhard et al. | |
| 6,894,289 B2 | 5/2005 | Nilson et al. | |
| 6,901,279 B2 | 5/2005 | Cable et al. | |
| 6,919,919 B2 | 7/2005 | Nelson et al. | |
| 6,922,246 B2 | 7/2005 | Nilson et al. | |
| 6,992,762 B2 | 1/2006 | Long et al. | |
| 7,177,024 B2 | 2/2007 | Nilson et al. | |
| 7,190,991 B2 | 3/2007 | Cable et al. | |
| 7,255,851 B2 | 8/2007 | Contag et al. | |
| 7,383,078 B2 * | 6/2008 | Cable et al. | 600/476 |
| 2003/0100998 A2 | 5/2003 | Brunner et al. | |
| 2004/0015085 A1 | 1/2004 | Soh et al. | |

FOREIGN PATENT DOCUMENTS

| | | | |
|---|---|---|---|
| JP | 04067615 A * | 3/1992 | |
| WO | WO 98/53300 | 11/1998 | |
| WO | WO 99/08233 | 2/1999 | |
| WO | WO 00/49938 | 8/2000 | |
| WO | WO 01/61324 | 8/2001 | |
| WO | WO 01/63247 | 8/2001 | |

OTHER PUBLICATIONS

Akana, "Chronic Cold in Adrenalectomized, Corticosterone (B)—Treated Rates: facilitated Corticotropin Responses to Acute Restraint Emerge as B Increases," Endocrinology, 1997. vol. 138, No. 8: 3249-3258.

Stanley, "Commercially available fluorometers, luminometers and imaging devices for low-light level measurements and allied kits and reagents: survey update 6," Luminescence, 1999. vol. 14:201-213.

Vesterberg, "A New Luminometer for sensitive quantification by chemiluminescence of specific proteins in microtitre plates and on blot membranes," Journal of Biochemical Biophysical Method, Nov. 30, 1995(4):301-14.

Notice of Allowance dated Mar. 21, 2008 from U.S. Appl. No. 10/914,971.

European Search Report dated Mar. 19, 2008 from EP Application No. 01913045.9.

Office Action dated May 13, 2008 from U.S. Appl. No. 11/142,564.

Yang, et al., *Whole-body optical imaging of green fluorescent protein-expressing tumors and metastases*, 1206-1211 PNAS, vol. 97, No. 3, Feb. 1, 2000.

Yang, et al., *Visualizing gene expression by whole-body fluorescence imaging*, 12278-12282 PNAS, vol. 97, No. 22, Oct. 24, 2000.

Reichman, *Handbook of Optical filters for Fluorescence Microscopy*, Chroma Technology Corp., HB1.1/Jun. 2000.

Mahmood, et al., Near-Infrared Optical Imaging of Protease Activity for Tumor Detection, *Radiology*, Dec. 1999, pp. 866-870.

Weissleder, et al., Shedding light onto live molecular targets, *Nature Medicine*, vol. 9, No. 1, Jan. 2003.

PCT patent application No. PCT/US01/06078, Written Opinion dated Jun. 14, 2002.

PCT patent application No. PCT/US01/06078, International Search Report dated May 22, 2002.

PCT patent application No. PCT/US01/06078, Preliminary Examination Report dated Sep. 12, 2002.

PCT patent application No. PCT/US03/05199, Written Opinion dated Dec. 11, 2003.

PCT patent application No. PCT/US03/05199, International Search Report dated Oct. 12, 2003.

European patent application No. EP 03713577.9-2204, Examination Report dated Feb. 20, 2006.

Australian Examination Report dated Aug. 6, 2008 in Australian Patent Application No. 2006236046.

Australian Examination Report dated Aug. 27, 2008 in Australian Patent Application No. 2006236048.

Australian Examination Report dated Jul. 30, 2008 in Australian Patent Application No. 2006236045.

EP application No. 03 713 577.9-2204, Examination Report dated Aug. 4, 2006.

VetEquip Incorporated website, http://www.vetequip.com/impac.htm IMPAC$_6$ An anesthesia system designed for high volume, assembly-line type procedures, Apr. 27, 2001, printed on 04/37/01.

VetEquip Incorporated website, http://www.vetequip.com/1807.htm Mobile Laboratory Animal Anesthesia System, Apr. 27, 2001, printed on Apr. 27, 2001.

Australian Examiner's First Report on patent application No. 2001241758, dated Nov. 18, 2004.

Office Action dated Sep. 17, 2009 in U.S. Appl. No. 11/142,564.
Office Action dated Mar. 9, 2009 in U.S. Appl. No. 11/142,564.
Office Action dated Dec. 23, 2008 in U.S. Appl. No. 11/142,564.
Office Action dated Jan. 22, 2010 in U.S. Appl. No. 11/142,564.
Final Office Action dated Dec. 9, 2010 in U.S. Appl. No. 11/139,323.
Final Office Action dated Dec. 10, 2010 in U.S. Appl. No. 11/139,107.
Final Office Action dated Mar. 8, 2011 in U.S. Appl. No. 11/139,107.
First Action Interview Pilot Program Pre-Interview Communication dated May 27, 2010 in U.S. Appl. No. 11/139,107.

Kobayashi et al., "Two-dimensional photon counting imaging and spatiotemporal characterization of ultraweak photon emission from a rat's brain in vivo", Journal of Neuroscience Methods 93 (1999), 163-168.

Levine, "Anoxic-Ischemic Ensephalopathy in Rats", The American Journal of Pathology, Jan. 1960, 1-17.

First Action Interview Pilot Program Pre-Interview Communication dated Jun. 11, 2010 in U.S. Appl. No. 11/139,323.

Final Office Action dated Jul. 13, 2010 in U.S. Appl. No. 11/142,564.

* cited by examiner

IMAGING APPARATUS WITH SELECTABLE MOVEABLE STAGE

CROSS-REFERENCE TO RELATED APPLICATION

This application is a divisional application of U.S. application Ser. No. 10/912,022, filed Aug. 4, 2004 now U.S. Pat. No. 6,901,279, by Michael D. Cable et al. and entitled, "Improved Imaging Apparatus," the content of which is hereby incorporated by reference herein, which in turn is a divisional application of U.S. application Ser. No. 09/795,056, filed Feb. 21, 2001 by Michael D. Cable et al. and entitled, "Imaging Apparatus", now issued as U.S. Pat. No. 6,775,567, the content of which is hereby incorporated by reference herein, which claims the benefit of: U.S. Provisional Patent Application No. 60/184,859 filed Feb. 25, 2000, naming M. D. Cable et al. as inventors, and titled "Light-Tight Specimen Chamber", which is incorporated by reference herein for all purposes.

FIELD OF THE INVENTION

The present invention relates generally to imaging systems. More specifically, the present invention relates to an imaging box which forms part of an imaging system used for imaging low intensity light sources, and also relates to numerous improvements to various components of an imaging box.

BACKGROUND OF THE INVENTION

One specialized type of imaging involves the capture of low intensity light—on the order of individual photons—from a light emitting sample. The source of the light indicates portions of the sample where an activity of interest may be taking place. For example, specialized in-vivo imaging applications may include analysis of one or more representations of emissions from internal portions of a specimen superimposed on a photographic representation of the specimen. The luminescence representation indicates portions of the specimen where an activity of interest may be taking place. The photographic representation provides the user with a pictorial reference of the specimen. Such imaging applications present particular challenges to the design of a box or chamber in which the sample is contained during imaging.

One particular challenge to imaging box design is the diverse lighting needs required during image capture. Photographic image capture typically requires the sample to be illuminated. Luminescent image capture requires substantially no light other than minute amounts produced within the sample. Conventional "light boxes", or "specimen chambers" have thus been developed to maintain the sample being imaged in relative darkness during luminescent image capture.

FIG. 1A is a fragmentary, rear elevation view of the inside of a latchable door 1 of a conventional light box, as seen from the interior of the box, showing a current latch mechanism 2. FIGS. 1B and 1C illustrate a seal 4 situated between the door 1 of FIG. 1A and the front wall of the box that the door is attached to. Collectively, the latch mechanism 2 and seal 4 allow a significant amount of light to enter the light box.

Thus, conventional imaging boxes or specimen chambers may not be adequate for many imaging applications, e.g., when the imaging involves the capture of low intensity light on the order of individual photons. In view of the foregoing, improved imaging apparatus would be desirable.

SUMMARY OF THE INVENTION

The present invention relates to an improved imaging apparatus that allow a user to perform numerous imaging operations. The present invention may include one or more improvements to imaging box design to improve illumination control within the imaging box, such as improved door seal arrangements, improved door closing mechanisms, and improved light seals between housing surfaces. The present invention may also include one or more improvements to imaging apparatus design to facilitate image capture, such as: an automated filter select device, automated focus control, f-stop adjustment and stage height, and improved internal illumination for capturing photographic images.

In one aspect, the present invention provides a box or chamber device that is substantially more "light-tight" than conventional light boxes, and thereby allows for more sensitive and accurate detection and imaging of low intensity light sources. The present invention also provides a variety of new features and improvements to the light box and accompanying imaging components to make the imaging process more convenient and accurate than was possible with "prior art" light boxes.

In another aspect, the present invention relates to an imaging box for capturing an image of a sample. The imaging box comprises a body including an interior cavity for receiving the sample and having a front wall defining an opening into the cavity. The imaging box also comprises a door having a rear wall, the door movable between an opened condition, enabling access to the interior cavity through the cavity opening, and a closed condition, positioning the rear wall substantially adjacent the body front wall to prevent access through the cavity opening. The door rear wall is adapted to cooperate with the front wall of the body, in the closed condition, to define a capture space extending substantially perimetrically about the cavity opening. The imaging box further comprises a compressible material disposed at least partially within the capture space, the compressible material having, when the door is in the closed position, a first side compressed substantially uniformly by the door rear wall and a second side compressed-substantially uniformly by the front wall.

In still another aspect, the present invention relates to an imaging box for capturing an image of a sample. The imaging box comprises a body including an interior cavity for receiving the sample, and having a front wall defining an opening into the cavity, the front wall also including a first wall extending outward from the front wall. The imaging box also comprises a door having a rear wall, the door movable between an opened condition, enabling access to the interior cavity through the cavity opening, and a closed condition, positioning the rear wall substantially adjacent the body front wall to prevent access through the cavity opening. The door also including a second wall skewed toward the front wall, the second wall adapted in a manner such that the second wall and the first wall substantially overlap, relative their respective depth, when the door is in the closed condition. The imaging box further comprises a compressible material disposed at least partially between the first wall and the second wall.

In yet another aspect, the present invention relates to an imaging box for capturing an image of a sample. The image box comprises a body including an interior cavity for receiving the sample, and having a front wall defining an opening into the cavity. The image box also comprises a door having a rear wall, the door movable between an opened condition, enabling access to the interior cavity through the cavity opening, and a closed condition, positioning the rear wall substantially adjacent the body front wall to prevent access through the cavity opening. The image box further comprises one of the body front wall and the door rear wall including a pair of generally parallel channel walls extending outwardly therefrom to form a channel extending substantially around the perimeter of the interior cavity opening when the door is in the closed condition. The image box additionally comprises a compressible material disposed in the channel. The image box also comprises the other of door rear wall and body front wall having an interengaging wall extending outwardly therefrom and adapted to extend into the channel in a manner such that the interengaging wall and the channel walls substantially overlap, relative their respective depth, when the door is in the closed condition, the interengaging wall further engaging the compressible material such that light entering the channel from the exterior of the body is intercepted by compressible material.

In another aspect, the present invention relates to an imaging box for capturing an image of a sample. The image box comprises a body including an interior cavity for receiving the sample, and having a front wall defining an opening into the cavity. The image box also comprises a door having a rear wall and an exterior face. The door movable is between an opened condition, enabling access to the interior cavity through the cavity opening, and a closed condition, positioning the rear wall substantially adjacent the body front wall to prevent access through the cavity opening. The image box further comprises a compressible material disposed on one of the rear wall and the front wall. The image box additionally comprises a first magnetic element attached to one of the rear wall and the front wall, the first magnetic element providing a first securing force between the door and the front wall when the door is in the closed condition.

In still another aspect, the present invention relates to an imaging box for capturing an image of a sample. The image box comprises a body including an interior cavity for receiving the sample and having a front wall defining an opening into the cavity. The image box also comprises a door having a rear wall and an exterior face, the door movable between an opened condition, enabling access to the interior cavity through the cavity opening, and a closed condition, positioning the rear wall substantially adjacent the body front wall to prevent access through the cavity opening. The image box further comprises a compressible material disposed on one of the rear wall and the front wall. The image box additionally comprises a user handle on the exterior face of the door. The image box also comprises a first latch operably positioned by the user handle and providing a securing force between the door and the front wall at a first location. The image box additionally comprises a second latch providing a securing force between the door and the front wall at a second location.

In yet another aspect, the present invention relates to an imaging system for capturing an image of a sample. The imaging system comprises an imaging box having a body including an interior cavity for receiving the sample and having a front wall defining an opening into the cavity. The imaging box also having a door with a rear wall and an exterior face, the door movable between an opened condition, enabling access to the interior cavity through the cavity opening, and a closed condition, positioning the rear-wall substantially adjacent the body front wall to prevent access through the cavity opening. The imaging system further comprises an optical filter select device adapted to carry a plurality of optical filters, the filter select device capable of selectively positioning one of the plurality of optical filters to intersect light emitted from the sample.

In another aspect, the present invention relates to an imaging system for capturing an image of a sample. The imaging system comprises an imaging box having a body including an interior cavity for receiving the sample and a front wall defining an opening into the cavity. The imaging system also comprises a door having a rear wall and an exterior face. The door movable between an opened condition, enabling access to the interior cavity through the cavity opening, and a closed condition, positioning the rear wall substantially adjacent the body front wall to prevent access through the cavity opening. The imaging system further comprises a moveable stage in the cavity interior that supports the sample, the moveable stage having a first vertical position and a second vertical position in the interior cavity, wherein the first vertical position and the second vertical position have the substantially same horizontal position in the interior cavity.

In still another aspect, the present invention relates to an imaging system for capturing an image of a sample. The imaging system comprises an imaging box having a body including an interior cavity for receiving the sample, and having a front wall defining an opening into the cavity. The imaging system also comprises a door having a rear wall and an exterior face, the door movable between an opened condition, enabling access to the interior cavity through the cavity opening, and a closed condition, positioning the rear wall substantially adjacent the body front wall to prevent access through the cavity opening. The imaging system further comprises a stage in the cavity interior configured to support the sample. The imaging system additionally comprises a gas manifold in the cavity interior and detachably coupled to the stage, the manifold including a first interface adapted to provide a gas to the sample. The imaging system also comprises a tube configured to transport the gas from outside the imaging box to the gas manifold.

In yet another aspect, the present invention relates to an imaging box for capturing an image of a sample. The image box comprises a body including an interior cavity for receiving the sample, and having a front wall defining an opening into the cavity. The image box also comprises a door having a rear wall, the door movable between an opened condition, enabling access to the interior cavity through the cavity opening, and a closed condition, positioning the rear wall substantially adjacent the body front wall to prevent access through the cavity opening. The image box further comprises at least one light tight seal, the seal comprising a first surface including a first channel, a second surface including a second channel, the first surface opposing the second surface such that the first channel and second channel at least partially face each other, and a compressible gasket disposed in the first and second channel, the gasket configured to contact opposing edges of the first and second channel when the first and second surfaces are in contact.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

I. Imaging System

Figure 2:
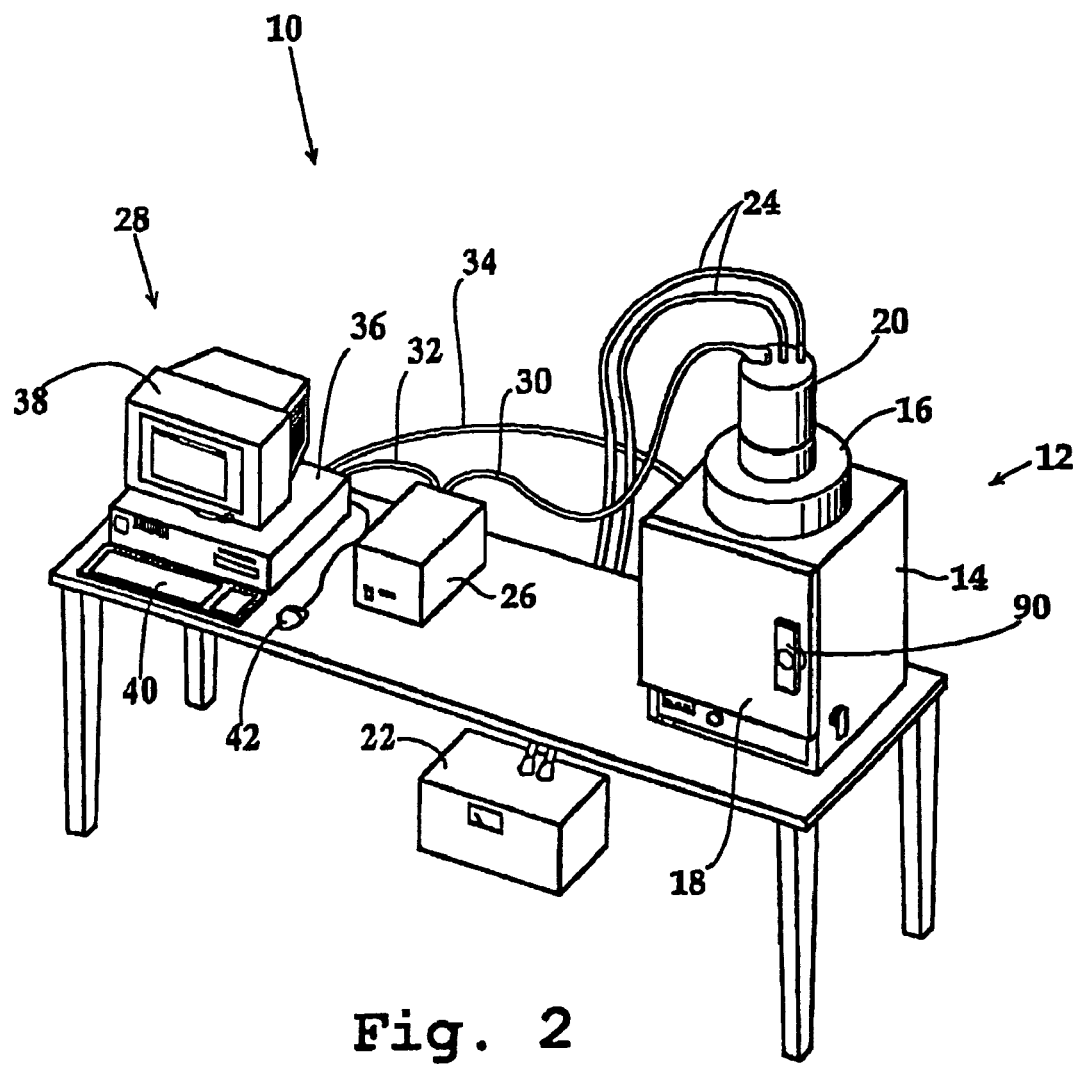
FIG. 2 is a perspective view of an imaging system including an imaging box, in accordance with one embodiment of the present invention.

In one aspect, the present invention relates generally to improved imaging systems. FIG. 2 illustrates an imaging system 10 configured to capture photographic and luminescence images in accordance with one embodiment of the present invention. The imaging system 10 may be used for imaging a low intensity light source, such as luminescence from luciferase-expressing cells, fluorescence from fluorescing molecules, and the like. The low intensity light source may be emitted from any of a variety of light-emitting samples which may include, for example, tissue culture plates, multi-well plates (including 96, 384 and 864 well plates), and animals or plants containing light-emitting molecules, such as various mammalian subjects such as mice containing luciferase expressing cells.

The imaging system 10 comprises an imaging box 12 adapted to receive a light-emitting sample in which low intensity light, e.g., luciferase-based luminescence, is to be detected. The imaging box 12 includes an upper housing 16 in which a camera lens is mounted. A high sensitivity camera, e.g., an intensified or a charge-coupled device (CCD) camera 20 is positioned on top of the imaging box 13 and positioned above, the upper housing 16. The CCD camera 20 is capable of capturing luminescent and photographic (i.e., reflection based images) images of the sample within the imaging box 12. The CCD camera 20 is cooled by a suitable source such as a refrigeration device 22 that cycles a cryogenic fluid through the CCD camera via conduits 24. A suitable refrigeration device is the "CRYOTIGER" compressor, which can be obtained from IGC-APD Cryogenics Inc., Allentown, Pa. Other methods, such as liquid nitrogen, may be used to cool the CCD camera 20.

An image processing unit 26 optionally interfaces between camera 20 and a computer 28 through cables 30 and 32 respectively. The computer 28, which may be of any suitable type, typically comprises a main unit 36 that typically contains hardware including a processor, memory components such as random-access memory (RAM) and read-only memory (ROM), and disk drive components (e.g., hard drive, CD, floppy drive, etc.). The computer 28 also includes a display 38 and input devices such as a keyboard 40 and mouse 42. The computer 28 is in communication with various components in the imaging box 12 via cable 34. To provide communication and control for these components, the computer 28 includes suitable processing hardware and software configured to provide output for controlling any of the devices in the imaging box 12. The processing hardware and software may include an I/O card, control logic for controlling any of the components of the imaging system 10, and a suitable graphical user interface for the imaging system 10. The computer 28 may also includes suitable processing hardware and software for the camera 20 such as additional imaging hardware, software, and image processing logic for processing information obtained by the camera 20. Components controlled by the computer 28 may include the camera 20, the motors responsible for camera 20 focus, the motors responsible for position control of a platform supporting the sample, the camera lens, f-stop, etc. The logic in computer 28 may take the form of software, hardware or a combination thereof. The computer 28 also communicates with a display 38 for presenting imaging information to the user. By way of example, the display 38 may be a monitor, which presents an image measurement graphical user interface (GUI) that allows the user to view imaging results and also acts an interface to control the imaging system 10.

A. Imaging Box

Figure 3:
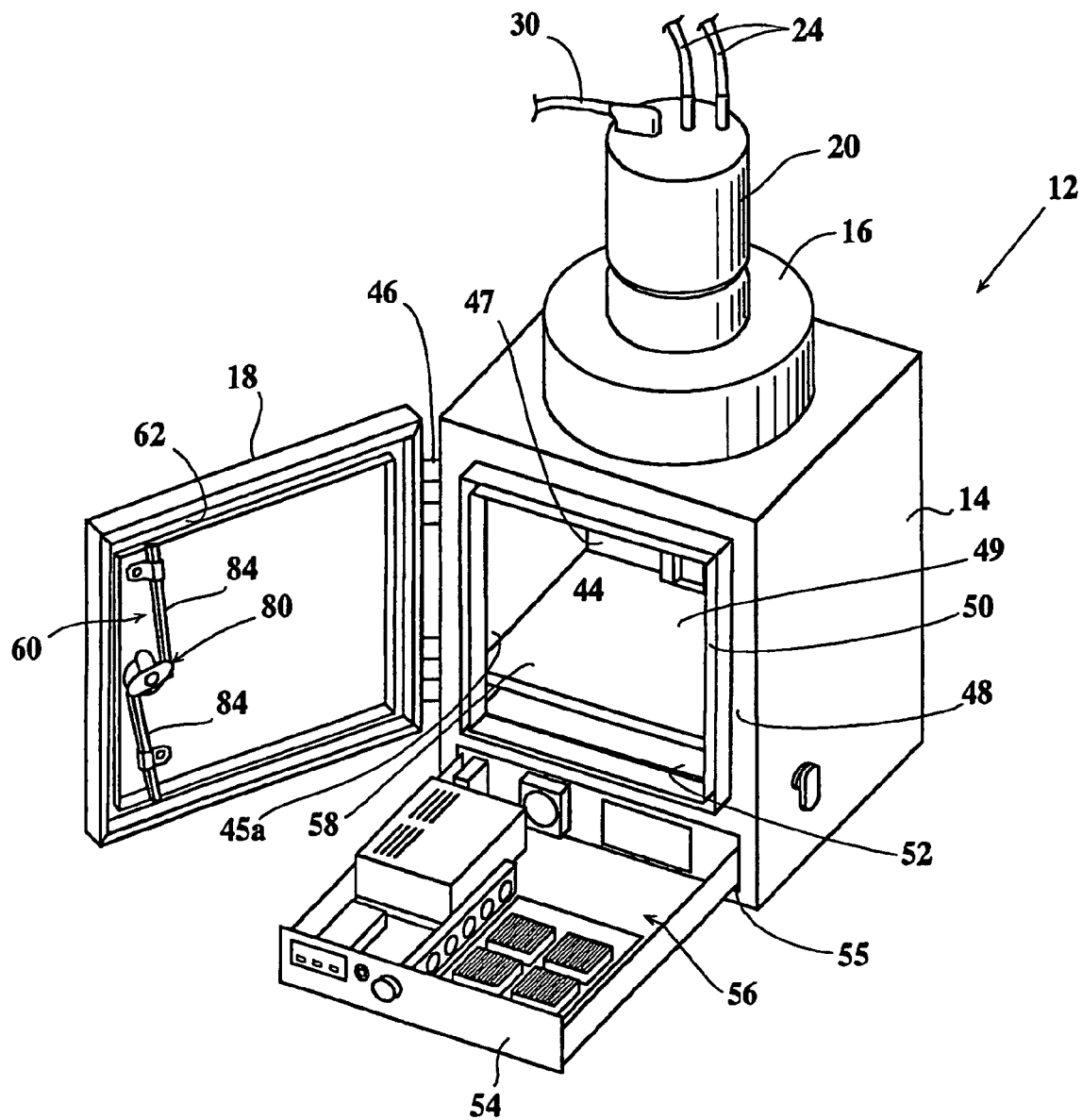
FIG. 3 is a perspective view of the imaging box and some attached imaging components of FIG. 2, with the imaging box door open and its electronics drawer pulled out.

In one aspect, the present invention relates to an imaging box suitable for various imaging operations. FIG. 3 illustrates the imaging box 12 of FIG. 2 in accordance with one embodiment of the present invention. The imaging box 12 is suitable for imaging including the capture of low intensity light on the order of individual photons, for example. The imaging box 12 substantially improves the control of imaging performed therein and is designed to improve the quality of the images generated from extremely low levels of light. In one embodiment, the imaging box 12 the quality of imaging by preventing the entry by light external to the imaging box in the ambient room. The imaging box 12 is referred to as "light-tight", e.g., it seals out essentially all of the external light from the ambient room from entering the box 12. The term "light-tight box" as used herein means a box or chamber device that seals out essentially all of the external light that would otherwise enter the box.

As shown in FIG. 3, the imaging box 12 includes a number of adaptations in accordance with the present invention. The imaging box 12 is illustrated with its door 18 open, showing an interior cavity 44 for receiving the sample. The interior cavity 44 is defined by opposing side enclosure panels 45*a* and 45*b* (45*b* not visible in FIG. 3), a light-tight partition 52 on the bottom, a top partition 103 (FIG. 10), a back enclosure panel 47, and a front wall 48 defining a cavity opening 49 into the interior cavity 44. Below the cavity 44 is a smaller compartment separated therefrom by the light-tight partition 52, the upper surface of which serves as a floor for the cavity 44. In one embodiment, the smaller compartment acts as a housing space and is adapted to slideably receive a drawer 54 though a front opening 55 formed in the body 14. The drawer 54 houses electronic components 56 which are in electrical communication with the computer 28 (FIG. 2) and control various components and functions of the box 14. In another embodiment, the imaging box 12 has a body 14 made of a suitable metal such as steel.

A latchable door 18 is pivotally attached to box body 14 by way of hinges 46 which permit the door 18 to be moved from the closed position as shown in FIG. 2 to the open position as shown in FIG. 3. In the open position, the door 18 enables user access to the cavity 44 through the opening 55. In the closed position, where an inside wall of the door 18 is substantially adjacent to the body front wall 48, the door 18 prevent access to the cavity interior 44 through the cavity opening 55. Although the hinges 46 may be of any suitable design, they are generally designed, made and installed to enable the door 18 to close properly to provide the required sealing characteristics, as will be explained below. In addition, although the imaging box is illustrated and discussed with only one door 18 for sake of brevity, the imaging box may comprise two or more doors for access to the interior cavity 44.

The body front wall 48 defines the cavity opening 49 to the interior cavity 44. Around the perimeter of the cavity opening 49, extending outwardly, generally perpendicular to front wall 48, is a second wall 50. In one embodiment, the second wall 50 extends substantially perimetrically around the cavity opening 49. The second wall 50 includes a distal edge portion positioned substantially adjacent the door rear wall when the door 18 is in the closed position. As will be explained in several embodiments below, the walls 48 and 50 cooperate with walls on door 18 to form a capture space around the perimeter of the cavity opening 49. This capture space substantially minimizes the amount of external light that can enter the cavity 44 when the door 18 is closed.

As shown in FIG. 3, the door 18 carries a latch mechanism 60 for securing the door 18 in the closed position. The door 18 also includes a compressible material 62 attached thereto for preventing light penetration by light in the ambient room. Thus, when the door 18 is closed and secured, a seal formed by cooperation between the door 18 and the body 14 creates a substantially "light-tight" seal for the cavity 44.

FIGS. 4, 5A, 5B, 5C and 5D illustrate different embodiments of a light-tight seal formed by cooperation between the door 18 and the body 14 in accordance with various embodiments of the present invention. Each of the seals 61*a*, 61*b*, 61*c* and 61*d* in FIGS. 5A, 5B, 5C and 5D, respectively, may include the compressible material 62. In one embodiment, the compressible material 62 is non-transparent, preferably black, and made from a resiliently deformable material. In a specific embodiment, the compressible material 62 is an elastomer having a modulus of elasticity of less than about 1000 psi. Preferably, the compressible material's modulus of elasticity is less than about 200 psi, and more preferably is less than about 100 psi. In another embodiment, the material has a durometer rating of between about 10 and about 50, and preferably between about 20 and 30.

Figure 4:
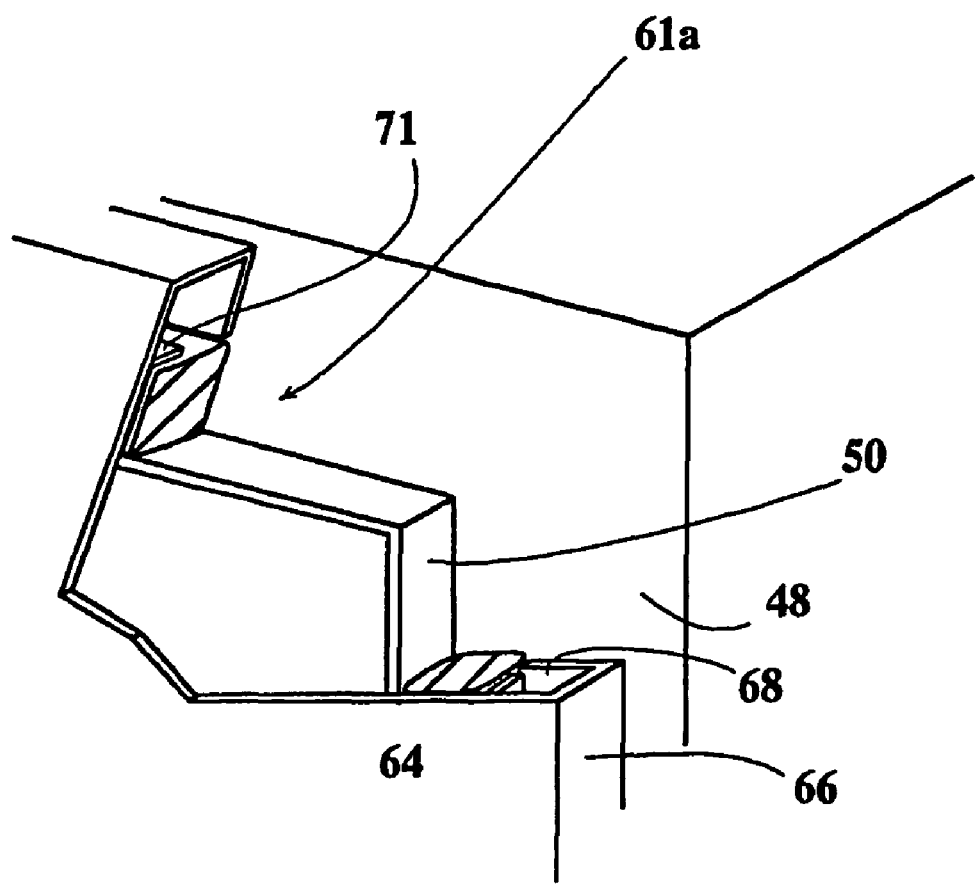
FIG. 4 is a front perspective view of part of the imaging box of FIG. 2 with a portion of the door cut away, illustrating a sealing arrangement in accordance with one embodiment of the invention.
Figure 5A:
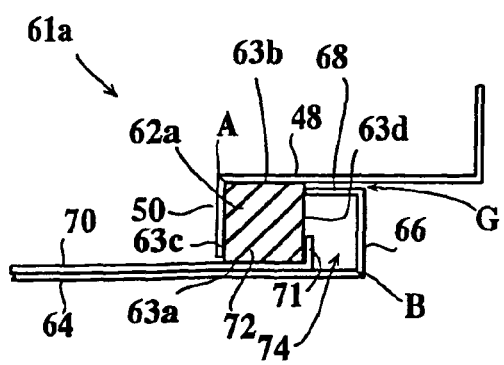
FIGS. 5A, 5B, 5C and 5D are cross-sectional views of parts of the door and front wall of the imaging box of FIG. 2, illustrating sealing arrangements in accordance with various embodiments of the invention.

FIGS. 4 and 5A illustrate a light-tight seal 61*a* between the door 18 and the body 14 walls 48 and 50 in accordance with one embodiment of the present invention. As shown, door 18 comprises a front wall 64, a rear wall 70, a side wall 66 and a second wall segment 68. The rear wall 70 is attached to the inner surface of the door front wall 64. In a specific embodiment, door rear wall 70 has a wall section 71 that extends substantially perimetrically around the cavity opening 49 when the door 18 is in the closed position. In another embodiment, the wall section 71 extends toward the body front wall 48 at an orientation engaging a fourth side portion 63*d* of the compressible material 62 between a second side portion 63*b* thereof engaged by the body front wall 48 and a first side portion 63*a* of the compressible material 62 engaged by the door rear wall 70.

As shown in FIGS. 4 and 5A, door walls 66, 68 and 70 cooperate with external surfaces on box walls 48 and 50 to define a capture space 72. Generally, the door 18 and box walls 48 and 50 may be arranged to form the capture space 72 having any polygonal cross-section. In this case, the capture space 72 has a rectangular cross-sectional area, as shown in FIGS. 4 and 5A, where a vertex A formed by box walls 48 and 50 opposes a vertex B formed by door walls 64 and 66.

The compressible material 62 is preferably disposed at least partially in the capture space 72 and compressed therein. In one embodiment, the compressible material 62 has a transverse cross-sectional dimension compressed at least partially by the body front wall 48 and at least partially by the door rear wall 70 when the door 18 is in the closed position. The door rear wall 70 is adapted to compress the compressible material 62 substantially along the entire first side portion 63*a* of the compressible material 62, and the body front wall 48 is adapted to compress the compressible material 62 substantially along the entire second side portion 63*b*, when the door 18 is in the closed position. Consequently, light entering the capture space from the exterior of the box 12 is intercepted by compressible material 62. In this case, the sides of the compressible material 62 being compressed by the door 18 and body 14 are positioned on opposite sides of the compressible material 62. It should be noted that the walls defining the capture space 72 may compress more than two sides of the compressible material 62. By way of example, the second wall 50 extending from the body front wall 48 is adapted to engage a third side portion 63c of the compressible material 62 extending between the first side portion 63a and the second side portion 63b.

In one embodiment, the capture space 72 and compressible material 62 both extend substantially perimetrically about the cavity opening 49. For example, in FIG. 5A, the dimensions and compressibility of the compressible material 62 are selected such that, when the door is closed, (i) each portion of the material 62 that contacts a door or box wall (i.e., box wall 48, second wall 50, and door rear wall 70) is compressed substantially uniformly along its contact portion, and (ii) there is a relatively small gap G between door wall 68 and front wall 48, such that the force exerted by the latch mechanism to retain the door 18 in the closed position is a consequence of contact with the compressible material 62 and not by contact between the door 18 and the box 12. The small gap G is provided by the compressible material 62 which is sized and dimensioned to prevent the door rear wall 70 from contacting the front wall 50 when the door 18 is in the closed condition.

The light seal 61 is thus formed by the material 62 pressing against one or more planar surfaces of the door 18 and body 14, thereby compressing substantially the entire perimetric sealing surface between the door 18 and the front wall 48 of the box 12. Accordingly, the door rear wall 70 and the body front wall 48 cooperate with the compressible material 62 to provide a light seal that causes light entering the capture space 72 to traverse the transverse the cross section of the material 62 for interception of the light thereof. The seal 61a thus greatly minimizes light penetration resulting from any interruptions in perimeter contact between the wall 50 and material 62a when the door 18 is closed.

Figure 1A:
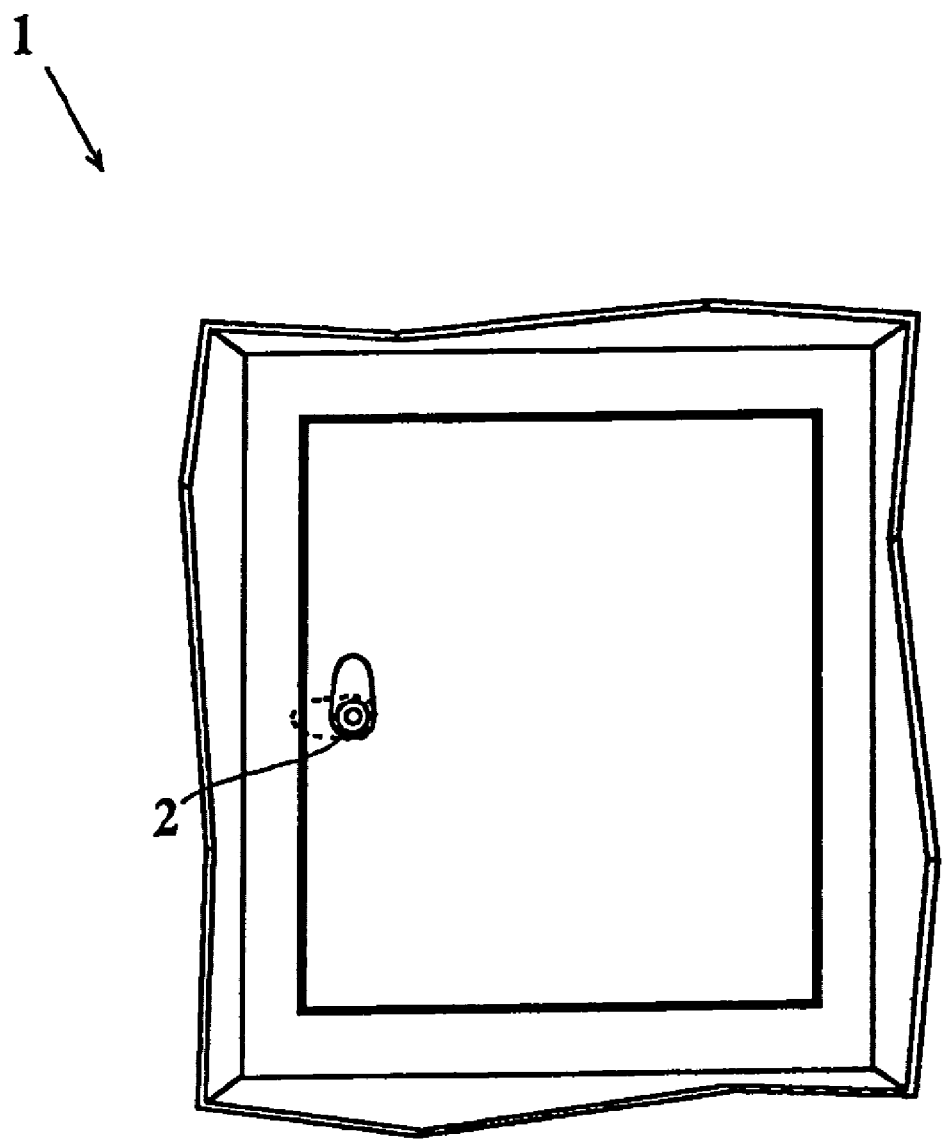
FIG. 1A is a rear elevation view of the inside of a latchable door of a conventional light box, as seen from the interior of the box, showing a current latch mechanism.
Figure 1B:
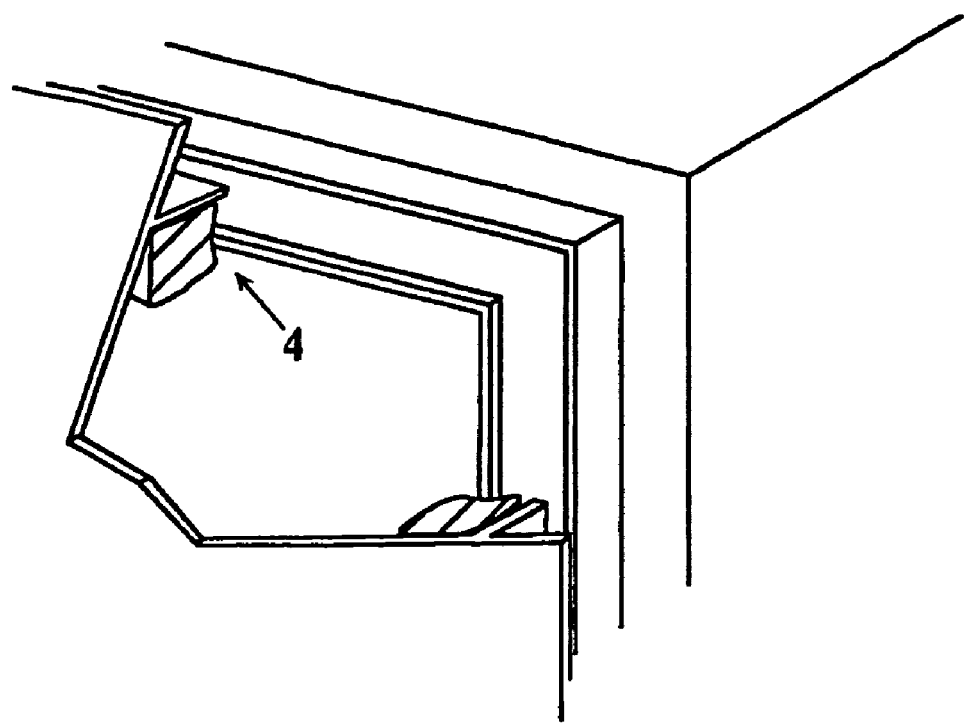
FIG. 1B is an enlarged perspective view, partially broken away, of a conventional seal used in the light box of FIG. 1A.
Figure 1C:
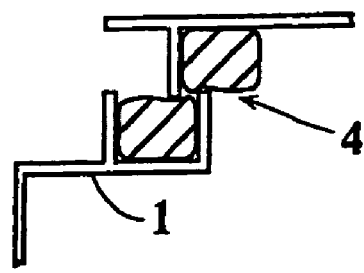
FIG. 1C is a top plan view, in cross-section of the conventional seal of FIG. 1B.

Referring back to FIG. 1C, experimentation performed by the applicants suggests that the seal 4 can be traversed by light making only slight deflections from a straight path. Accordingly, any defects in the seal 4 along its length can result in a significant amount of light entering the box.

To further reduce light penetration, the capture space 72 of FIG. 5A introduces two right angles that light would need to negotiate before it could enter the interior cavity 44 from the outside. Any light passing between front wall 48 and second wall segment 68 would thus be required to traverse at least two right angle turns before reaching the interior side of wall 50. Moreover, since the compressible material 62 is also preferably disposed at these right angle turns, such light would be intercepted by the disposed material. This design therefore advantageously improves the light barrier between the cavity 44 and the ambient room.

In the embodiment illustrated in FIGS. 4 and 5A, the compressible material 62a is rectangular-shaped in cross-section (e.g., about 0.75 in. by 0.5 in.) and has a solid core. By way of example, the compressible material 62 may be made of an adhesive backed closed cell foam having a density of between about 7 to about 9 lbs./cu. ft. and a compressibility of about 25% deflection at 5 to 9 psi. Typical of such materials is produced by Rogers of Decatur, Ill. In another embodiment, the material 62b is opaque with a light absorbing surface.

In addition to the light barrier provided by the capture space 72 and the compressible material 62a, the door side wall 66 and second wall segment 68 also function to prevent light penetration into the interior cavity 44. The side wall 66 is attached to the front wall 64 of the door and extends outwardly therefrom toward the body front wall 48. The side wall 66 is skewed toward the front wall 48 of the box 12 and is adapted such that the side wall 66 substantially overlaps the second wall 50 relative their respective depths when the door 18 is closed. Thus, a distal edge portion of the second wall 50 is positioned substantially adjacent the door rear wall 70, and a distal edge portion of the door side wall 66 is positioned substantially adjacent the body front wall 48. Preferably, the side wall 66 extends substantially perimetrically around the opening 49 and substantially perimetrically outside and generally parallel to the second wall 50 when the door 18 is in the closed position. In another embodiment, the side wall 66 extends toward and substantially perpendicular to the box front wall 48 when the door 18 is closed.

Extending from the distal portion of the side wall 66 is the second wall segment 68 which is also substantially adjacent and preferably parallel to the body front wall 48 as shown in FIG. 5A As previously indicated, the compressible material 62 is sized to create a relatively small gap G between the distal edge portion of side wall 66 and front wall 48 which prevents the door rear wall 70 from contacting the front wall 50 when the door 18 is in the closed condition. In one embodiment, this gap G is in the range of about 1/1000 inches to about ½ inches. In a more specific embodiment, the small gap G is in the range of about 1/1000 inches to about ⅛ inches.

Figure 5B:
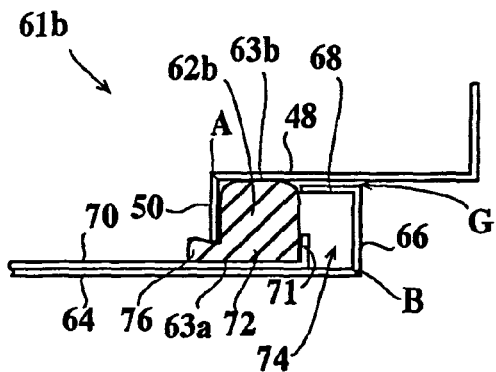

Referring now to FIG. 5B, a light-tight seal 61b is formed between the door 18 and the body 14 walls 48 and 50 in accordance with another embodiment of the present invention. In this embodiment, the compressible material 62b is also disposed in the capture space 72 (formed by walls 48, 50, 70 and 71). Similar to the embodiment of FIG. 5A, the compressible material is compressed along its opposite sides 63b and 63a by walls 48 and 70, respectively. In addition, the compressible material 62b includes a ledge portion 76 which protrudes between the distal portion of box second wall 50 and the door wall 70 to extend into the box cavity 44 when the door 18 is in the closed position. In this case, the second wall 50 is shortened and its distal portion compresses the ledge portion 76 outside the capture space 72 to provide additional light sealing. More specifically, upon closing the door 18, the ledge portion 76 is compressed by the distal portion of box wall 50 and door wall 70. The material 62b with its custom profile may be custom-made by a suitable seal or gasket manufacturer such as EPM, Inc., Stockbridge, Ga. In one embodiment, the material 62b is made of solid rubber having a durometer between about 20 and about 30, such as ethylene propylene diene monomer (EPDM) or styrene-butadiene rubber (SBR).

Figure 5C:
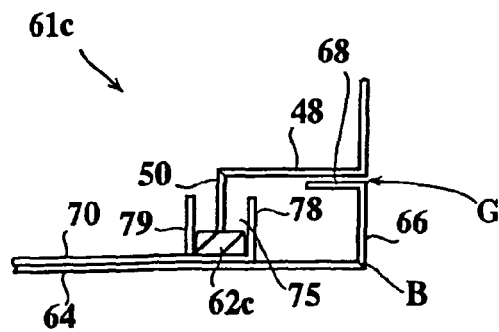

FIG. 5C illustrates yet another light-tight seal 61c in accordance with another embodiment of the present invention. The seal 61c includes a channel 75 formed by generally parallel channel walls 78 and 79 which extend outwardly from the door 18 toward the box front wall 48, and further extend perimetrically about the cavity opening 49 when the door 18 is in the closed condition. A compressible material 62c is disposed in the channel 75. The box second wall 50, extending outwardly from the front wall 48, is adapted to extend into the channel 75 in a manner such that the second wall 50 and the channel walls 78 and 79 substantially overlap, relative their respective depth, when the door 18 is in the closed condition. In addition, the channel walls 78 and 79 and the interengaging second wall 50 are, preferably substantially parallel to one another when the door 18 is in the closed condition.

In one embodiment, the dimensions and compressibility of the compressible material 62c of FIG. 5C are selected such that, when the door 18 is closed and latched, the material 62*c* is relatively uniformly compressed around the perimeter of the cavity opening 49 when the distal portion of the box second wall 50 contacts the material. Further, the compressible material is sized to form the small gap G between door wall 68 and front wall 48, such that the force exerted by the latch mechanism to retain the door 18 in the closed position is dispersed by the material 62*c*. In this case, the light seal 61*c* is formed when the distal portion of the box wall 50 compresses the material against the door wall 70. As a result, the geometry of the overlap requires light entering the channel 75 from the exterior of the body 14 to be intercepted by the compressible material 62*c*. In one embodiment, the compressible material 62*c* has a thickness of at most ¾ of the depth of the channel 75, and preferably at most ½ of the depth of the channel 75.

It should be noted that in the structural arrangement of FIG. 5C, a light-tight seal may still be formed without the compressible material 62*c*. This is due to the geometry of the spaced-apart channel walls 78, 79 and the interengaged second wall 50, and their spatial relationships, in the closed position. Any ambient light entering through Gap G must negotiate the maze formed between these interengaged walls. As viewed in FIG. 5C, such diffused light must traverse at least three right angle turns created by the walls before it can enter the interior cavity 44.

Although the channel walls 78 and 79 are on the door 18 and the interengaging second wall 50 is on the opposing front wall 48, it will be understood that the channel walls may be placed on the front wall 48 and the opposing interengaging wall situated on the door 18. Further, it will be appreciated that the seal 61 according to the present invention may contain two or more such channels and interengaging walls to improve light protection for the interior cavity 44.

Figure 5D:
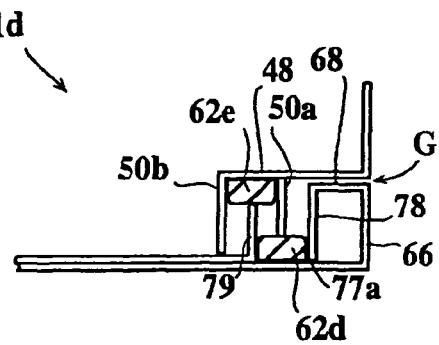

FIG. 5D illustrates such a light-tight seal 61*d* which includes first and second compressible materials 62*d* and 62*e*, retained inside two channels 77*a* and 77*b*, respectively. The channel 77*a* is formed by channel walls 78 and 79, both of which extend from the door 18 similar to the light-tight seal 61*c*. The channel 77*b* is formed by generally parallel channel walls 50*a* and 50*b*, both of which extend from the front wall 48 of the box 12 and substantially perimetrically around the cavity opening 49. In this case, the channel wall 79 is received in the channel 77*b* when the door 18 is in the closed condition. Thus, the channel wall 79 engages the second compressible material 62*e* such that light entering the second channel 77*b* from the exterior of the body 14 is intercepted by the second compressible material 62*e*.

The materials 62*d* and 62*e* fill only a portion of the channels 77*a* and 77*b* respectively, e.g., at most about ¾ of the channel 75 depth as measured from the walls 70 and 48 respectively, preferably at most about ½ the channel depth, and more preferably at most about ¼ the channel depth. Thus, the interengaged walls 50*a* and 50*b* and channel walls 78 and 79 substantial overlap, relative their respective depth, when the door 18 is closed. Any light attempting to penetrate the light barrier would require at least six right angle turns (including four through the compressible materials 62*d* and 62*e*) before it can enter the interior cavity 44 from the ambient room.

Similar to the embodiments illustrated in FIGS. 5A and 5B, the door 18 of FIGS. 5C and 5D further includes door side wall 66 extending outwardly from the door 18 toward the front wall 48 when the door is in the closed position. In this case, the door side wall 66 is positioned perimetrically outside and generally parallel to the channel walls 78 and 79 and the interengaging front wall 50. The door 18 further includes the second wall segment 68 extending from the door side wall 66, and oriented substantially adjacent to the front wall 48 when the door 18 is in the closed condition. As shown, the second wall segment 68 extends in the inward direction toward interengaging front wall 50 and the channel walls 78 and 79.

In another aspect of the present invention, several designs for securing the door 18 are provided that minimize light penetration from the ambient room. Referring back to FIGS. 1A-C, experimentation performed by the applicants suggests that the securing force provided by the latch mechanism 2 when the door 1 is closed may also lead to additional undesired light entering the box. When the door 1 is closed, the latch mechanism 2 provides a localized securing force at a single point along the door 1 (i.e., at the point of contact between the latch mechanism 2 and the door 1). This localized force provides an inconsistent pressure along the seal 4 and may lead to gaps in the seal 4 and other light sealing inconsistencies around the perimeter of the box 12.

As shown in FIGS. 6A-6D, latch mechanisms 60*a-d* for securing the door 18 in accordance with various embodiments of the present invention. The latch mechanisms 60*a-d* include multiple points of contact between the door 18 and the box 12 to provide more uniform force distribution across for the seal 61. This more uniform distribution minimizes light penetration resulting from any inconsistencies in perimeter contact between the wall 50 and material 62 when the door 18 is closed.

Figure 6A:
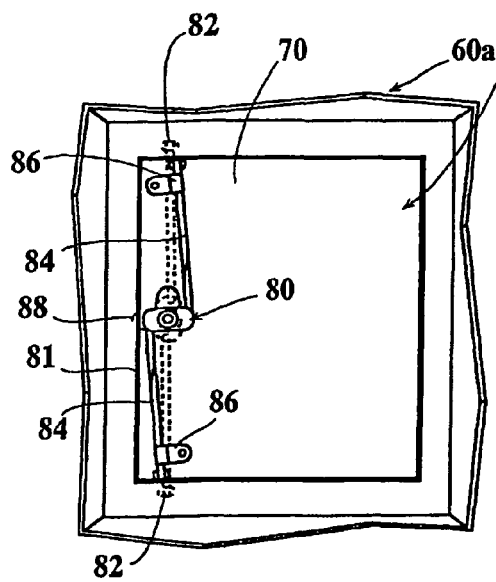
FIGS. 6A, 6B, 6C and 6D are fragmentary rear elevation views that illustrate the inside of the door, as seen from the interior of the imaging box of FIG. 2, showing latch mechanisms in accordance with various embodiments of the present invention.

FIGS. 3 and 6A illustrate the latch mechanism 60*a* in accordance with one embodiment of the present invention. The latch mechanism 60*a* includes a plurality of latches 86 located on the inside of the door 18. Each latch 86 is moveable between a first position, disengaged with the front wall 48, and a second position, engaged with the front wall 48 in which a securing force is applied between the door 18 and the front wall 48 at a strategic location. Together, the latches 86 provide a multi-point seal between the compressible material 62 in the door 18 and box walls 48 and 50 and distribute the applied compressive closing force along the vertical non-hinged edge 81 of the door. This multiple contact provides a substantially uniform securing and compression force against the compressible material 62 and along the vertical non-hinged edge 81 between the latches 86.

The latch mechanism 60*a* includes a main latch 80 and two dependent latches 82, each of which is moveably linked to the main latch 80 by rods 84. The rods 84 are each slideably supported by stays 86 which are mounted to the rear wall 70 of the door 18. The main latch includes a latch element 88 rotatably mounted on the inside of the door 18 for applying a force against the box 12. A handle 90 (see FIG. 2) extends from the exterior face of the door 18 to enable user manipulation. The handle 90 permits a user to operably position the latch element 88 and each of the dependent latches 82 between the first position, where the latches are disengaged with the inner surface of wall 48 (solid lines in FIG. 6A), and the second position, where the latches are engaged (broken lines in FIG. 6A). In one embodiment, the latch element 88 and dependent latches 82 may have a tapered engaging surface that contacts the wall 48 and provides a controllable amount of force which increases as the rotation of the handle 90 increases. In another embodiment, the main latch does not include a latch element 88 and the dependent latches 82 each comprise a rectangular element that applies the securing force between the door 18 and the box 12. Such a configuration is commercially available from Doortronics Systems, Inc. of Sag Harbor, N.Y.

Figure 6B:
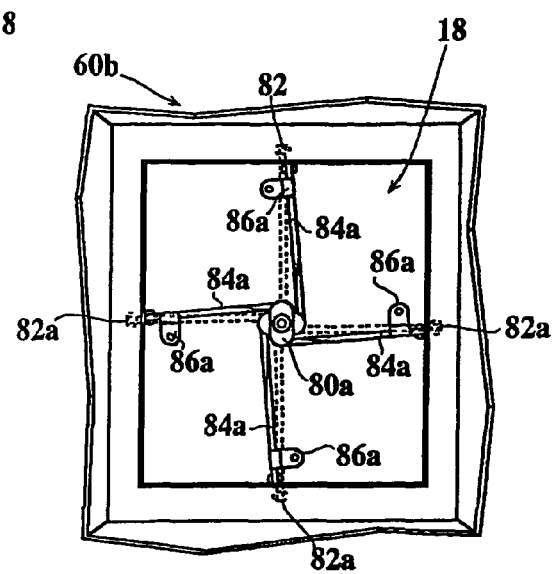

FIG. 6B illustrates another latch mechanism 60b in accordance with one embodiment of the present invention. The latch mechanism 60b includes a plurality of spaced-apart latches 82 disposed along the inside of the door 18 to provide a multi-point seal against the compressible material 62 between the door 18 and box walls 48 and 50. This arrangement uniformly distributes the compressive force when the door 18 is closed substantially about the perimeter of the box opening 49. This is performed by providing four dependent latches 82a distributed on four different edges of the door. Each dependent latch 82a is moveably linked by individual rods 84a to a cam device 80a which is rotatably mounted to the center of the door 18. These rods 84a are each slideably supported by stays 86a mounted to the inside of the door 18. With this arrangement, the cam device 80a does not have a latch element that engages to the box 12, such as the latch element 88 of the embodiment of FIG. 6A An external knob, however, is included for user manipulation and simultaneously actuating the four dependent latches 82 between engaged and disengaged positions. In one embodiment, the dependent latches 82 may have a tapered engaging surface that contacts the wall 48 in order to provide a controllable amount of force when securing the door 18.

Figure 6C:
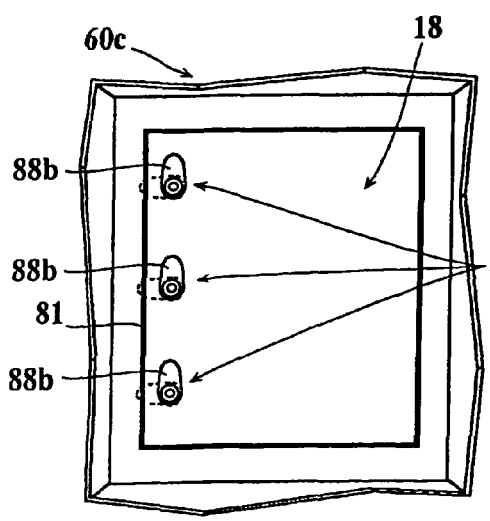
Figure 6D:
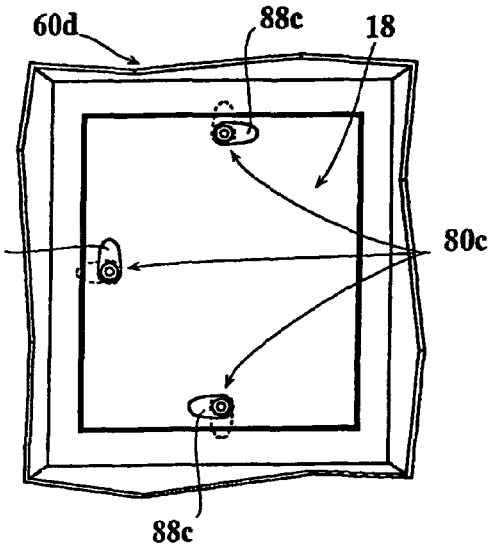

Referring now to FIGS. 6C and 6D, latch mechanisms 60c and 60d are illustrated in accordance with other embodiments of the present invention. In both embodiments, at least three latches 80b and 80c, respectively, are provided, each with their own independently controllable external handle. These latches are spaced-apart at strategic locations about perimeter of the door 18 and box opening 49. Each latch 88b, 88c is moveable between a first position, disengaged with the front wall 48 (solid lines in FIGS. 6C and 6D), and a second position, engaged with the front wall 48 in which a securing force is applied between the door 18 and the front wall 48 (broken lines in FIGS. 6C and 6D). In the latch mechanism 60c embodiment, the latches 88b are spaced-apart along the vertical edge 81 of the door opposite the door hinges. Collectively, the latches 88 provide securing forces which uniformly compress the compressible material 62 substantially between each pair of latches 88 along the vertical edge 81 of the door 18. In the latch mechanism 60d embodiment, in contrast, the latches 88c are spaced-apart along different door 18 edges. Each latch 88c is equipped with its own user handle to operably position its corresponding latch 88 between the disengaged first position (solid lines in FIG. 6D), and the engaged second position (broken lines in FIG. 6D). Similarly, the latch element may have a tapered engaging surface which provides a controllable amount of force which increases with increased rotation of its external knob.

Figure 6E:
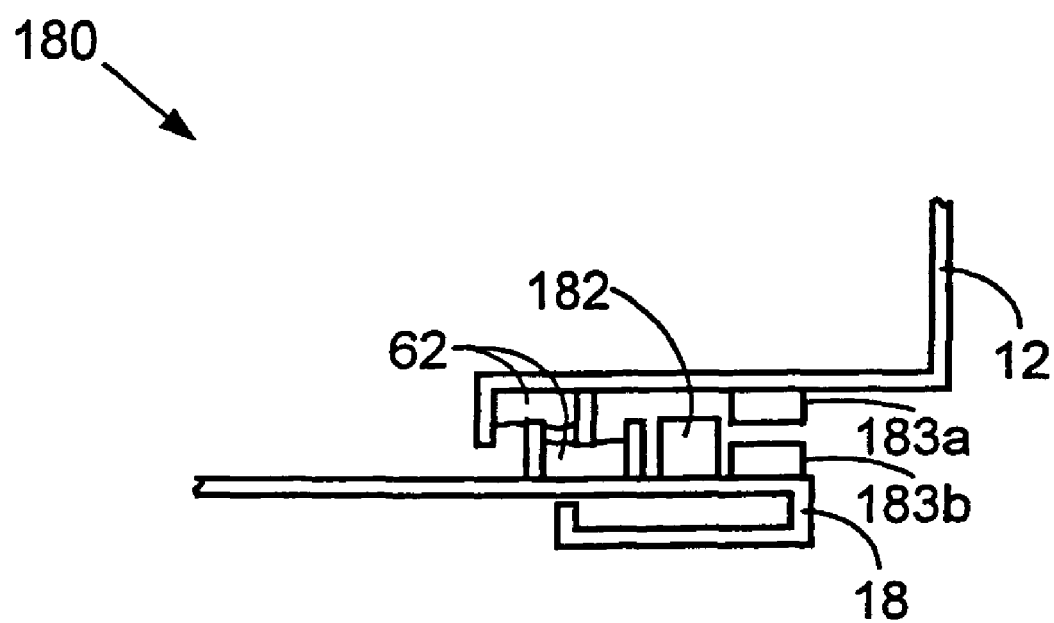
FIG. 6E illustrates a magnetic latch mechanism for securing the door of FIG. 2 in accordance with another embodiment of the present invention.

FIG. 6E illustrates a latch mechanism 180 for securing the door 18 of FIG. 2 in accordance with another embodiment of the present invention. The latch mechanism 180 includes a magnetic element 182 attached to the box 12 front wall. The magnetic element 182 provides a securing force between the metal door 18 and the front wall when the door 18 is in the closed condition. In a specific embodiment, the magnetic element 182 is a permanent magnet that provides a securing force large enough to compress the compressible material 62 and to keep the door from inadvertently opening when someone brushes the door 18 or other similar small forces that may open the door 18. In a specific embodiment, the magnetic element 182 is a permanent magnet that generates a securing force in the range of 25-30 lbf. In another embodiment, the latch mechanism 180 includes a second magnetic element, similar to the magnetic element 182, attached to the box 12 front wall at another point on the box 12 face. Together, the two magnetic elements provide a multi-location closing mechanism that distributes the applied compressive closing forces along the perimeter of the door 18. This multi-location magnetic latch provides a substantially uniform securing and compression force against the compressible material 62 and along the door 18 between the magnetic elements.

In another embodiment, the latch mechanism 180 includes an electromagnet 183a and 183b attached on facing surfaces of the door 18 and the box 12 front wall. The electromagnet 183 provides a securing force between the metal door 18 and the front wall when the door 18 is in the closed condition. The securing force provided by the electromagnet 183 is large enough to keep a user from opening the door 18. In a specific embodiment, the electromagnet is only powered during luminescent image capture of the sample, thus preventing the door 18 to be accidentally or inadvertently opened during luminescent image capture.

Figure 7:
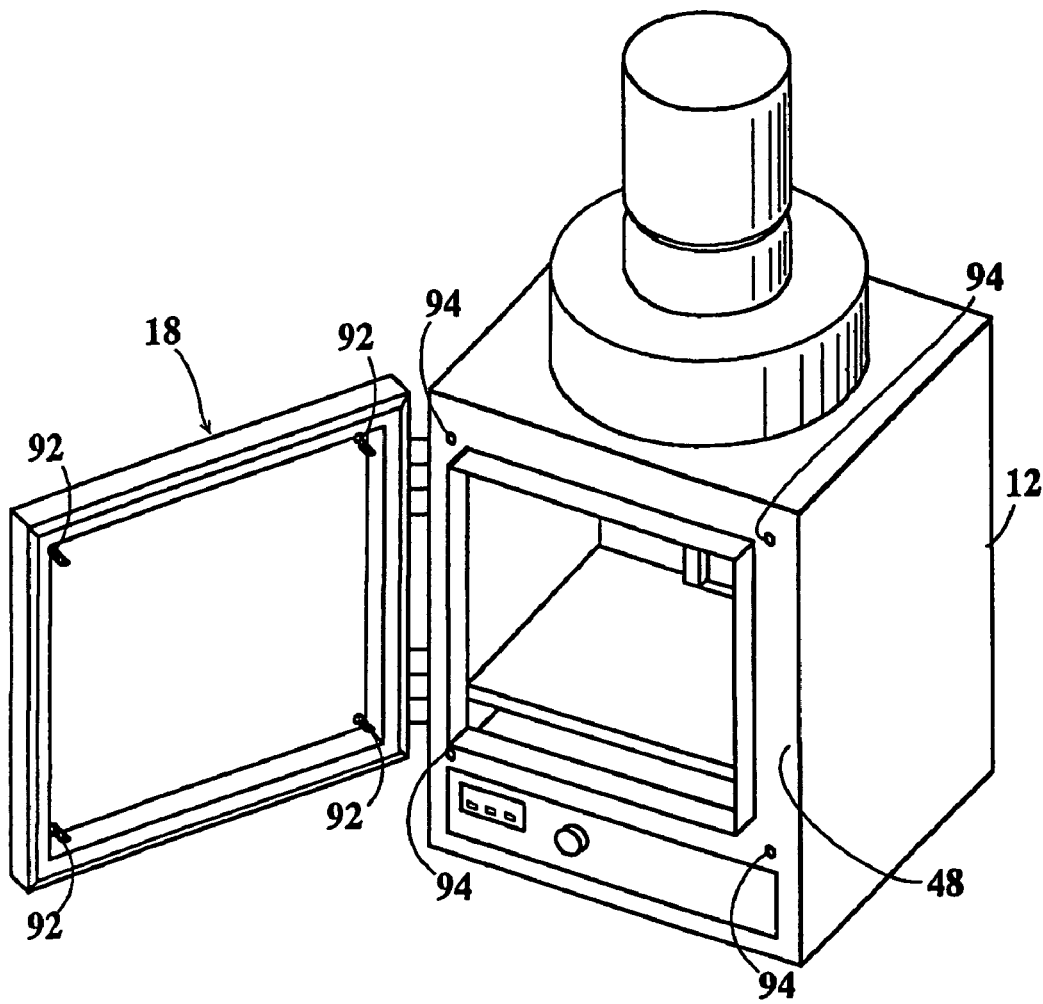
FIG. 7 is a perspective view of the imaging box of FIG. 2 with its door open, showing a uniform pressure applying mechanism, in accordance with another embodiment of the present invention.
Figure 8:
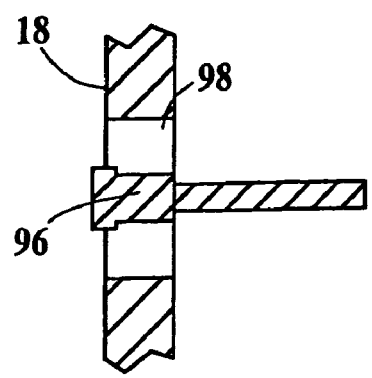
FIG. 8 is a fragmentary cross-sectional view of the door of the imaging box of FIG. 7, illustrating a portion of the uniform pressure applying mechanism in accordance with one embodiment of the present invention.

FIGS. 7 and 8 illustrate a mechanism for securing the door 18 in accordance with another embodiment of the present invention. A plurality of screw latches 92 are spaced about the perimeter of the door 18 and configured to engage with corresponding threads 94 in wall 48 of the box 12. When the door 18 is in the closed position, the screw latches 92 contact their corresponding threads 94. Each screw 92 is then driven by an individual worm-drive stepper motor 96 to apply a predetermined amount of pressure to the compressible material 62 disposed between the door 18 and the wall 48A pressure transducer 98 communicates with each motor 96 and is programmed to stop the motor when the predetermined amount of pressure is reached. The transducers 98 may be coupled to the computer 28, and may be, programmed to be conveniently adjust the properties thereof through keyboard 40 and/or mouse 42.

Advantageously, the design of the seal 61 and the distributed manner in which the seal 61 is engaged when the door 18 is closed provide a substantially more light-tight imaging box than was previously available, as evidenced by the comparison testing described below. Having briefly discussed various illumination control improvements of the imaging box 12, numerous other aspects of the imaging box 12 will now be discussed.

Figure 9:
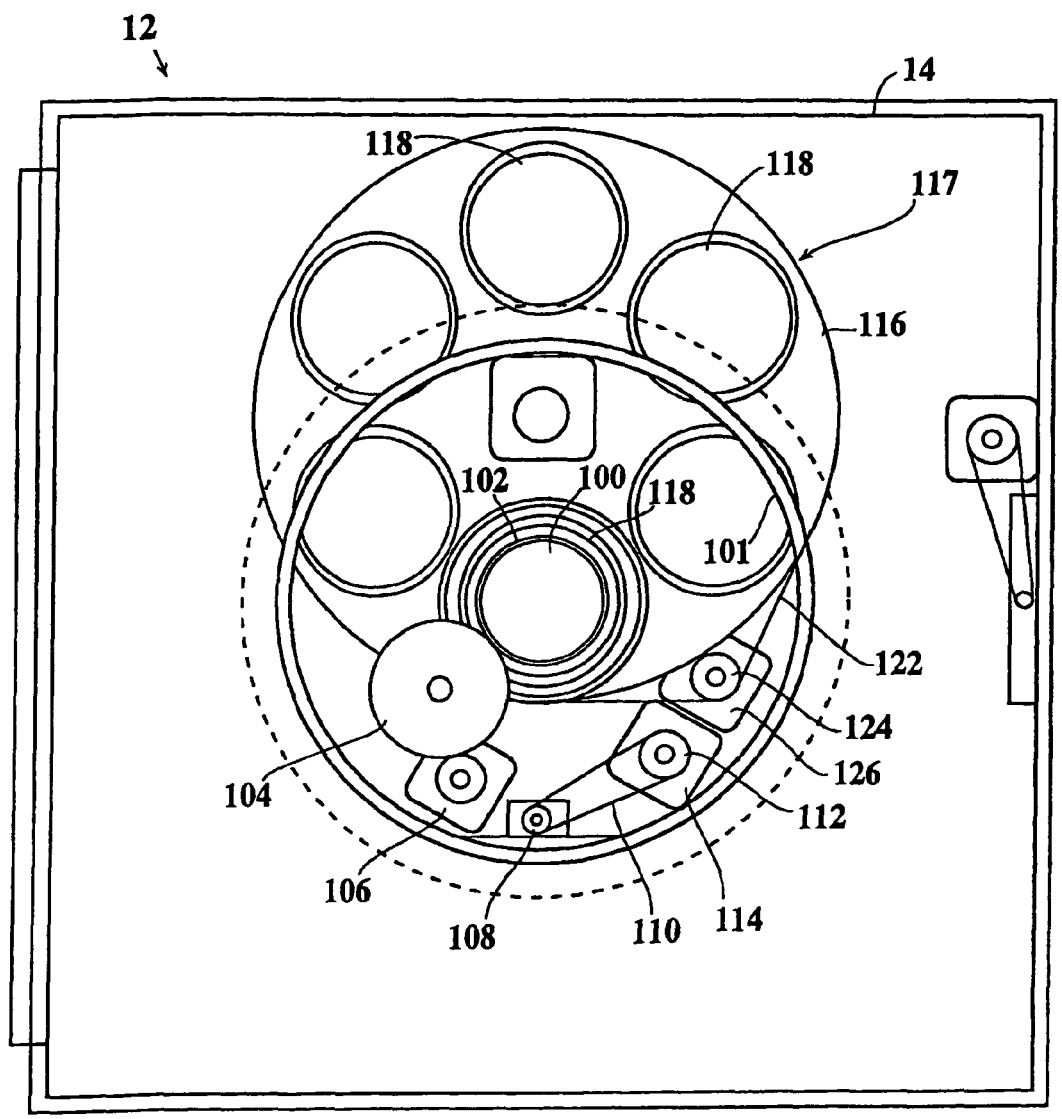
FIG. 9 is a bottom plan view, cut-away, of the imaging box of FIG. 2, illustrating various imaging components in accordance with one embodiment of the present invention.
Figure 10:
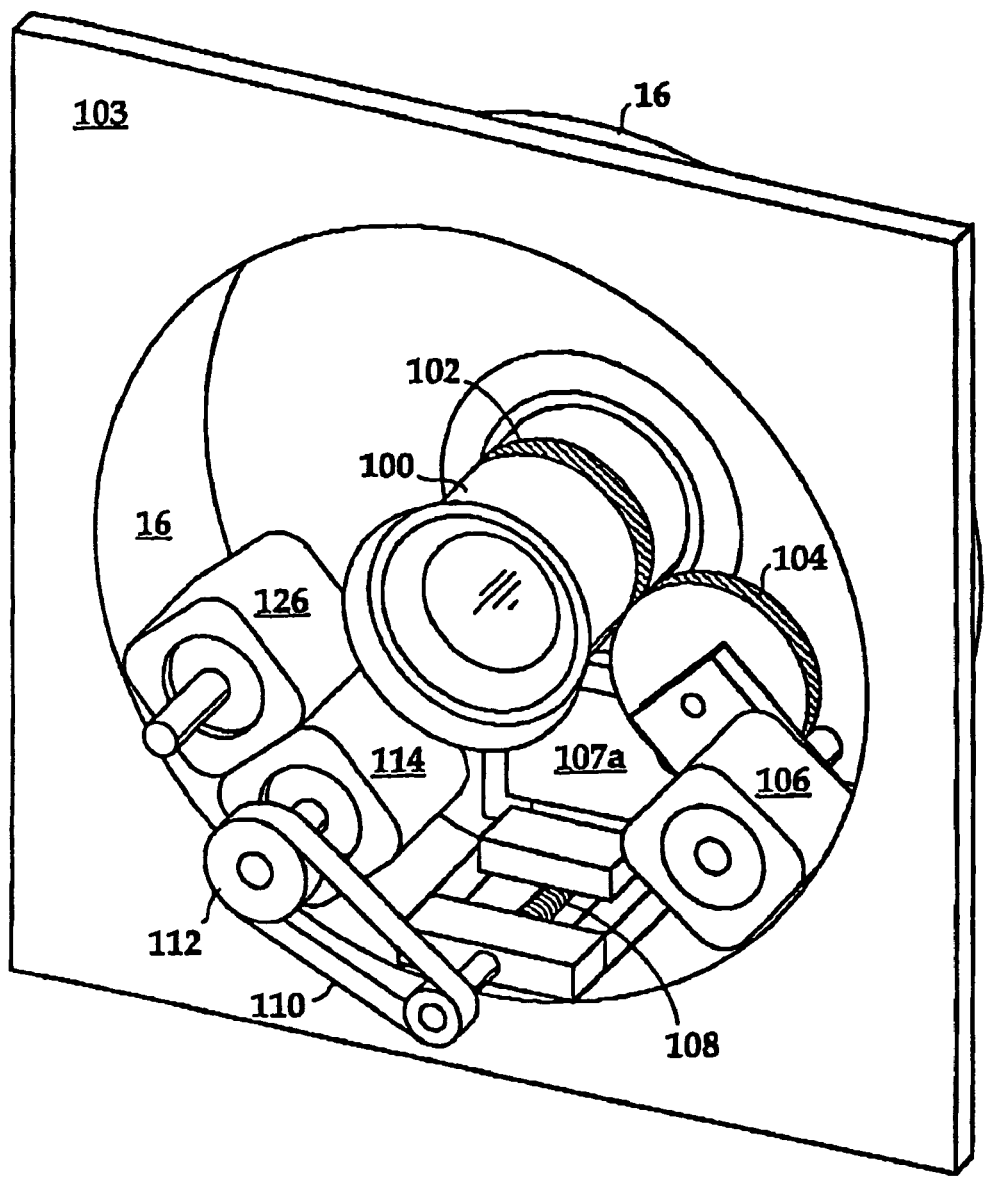
FIG. 10 is a perspective view of selected imaging components included in the imaging box of FIG. 2 in accordance with one embodiment of the present invention.
Figure 11:
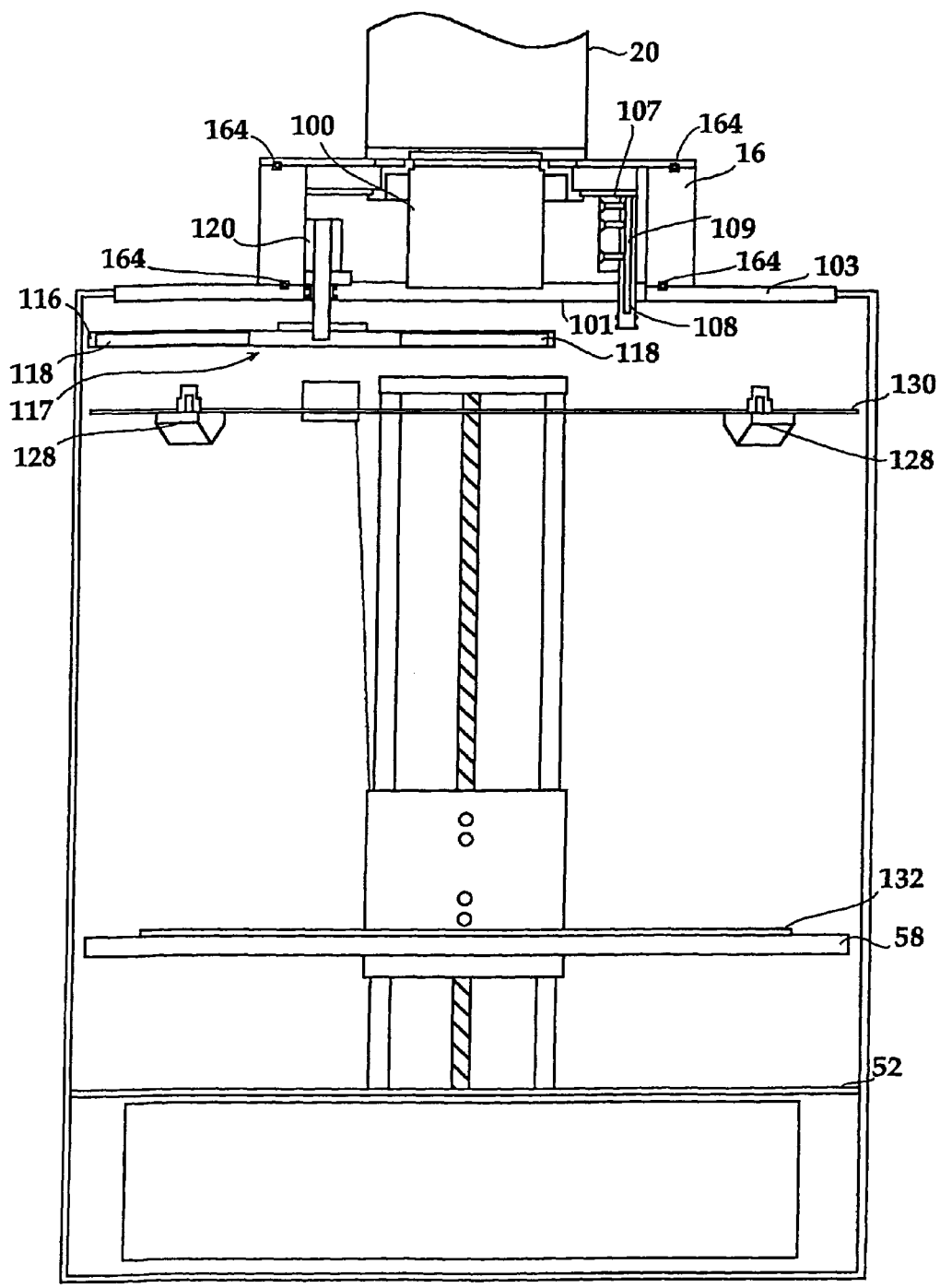
FIG. 11 is a front elevation view, in cross-section, of the interior of the imaging box of FIG. 2 and associated imaging components.

Referring now primarily to FIGS. 9, 10 and 11, various components housed in the upper portion of the box 12 will now be detailed. FIG. 9 is a bottom view of the components in the upper portion of the box 12 with the top face of the box 12 cut away. FIG. 10 is a perspective view of selected imaging components in the upper portion of the box 12. FIG. 11 is a cross-sectional side view of the box 12 looking into the cavity 44 with various components in the upper portion of the box 12 shown in cross-section.

The system 10 provides user automated control of image capture in the box 12. Referring to FIGS. 9 and 11, a camera lens 100 is mounted in upper housing 16, with the lens 100 in view of the interior cavity 44 through a hole 101 formed in a top plate 103 of the box 12. The camera lens 100 is optically coupled to the camera 20 of FIG. 3. and includes a user controlled aperture or F-stop ring 102 for adjusting the F-stop or aperture of the lens 100, thereby modulating the amount of light passing through the lens. By way of example, a Navitar, f 0.95, 50 mm TV lens is suitable for use as the camera lens 100. The F-stop ring 102 includes circumferentially disposed teeth that engage a gear 104 driven by an F-stop motor 106. The F-stop motor 106 is in electrical communication with the electrical components 56 and controlled by computer 28. Together, the motor 106 and processor in computer 28 act to position the f-stop of the lens 100.

Also associated with the camera lens 100 is a focusing mechanism including lens support 107 for supporting and focusing the lens 100 to provide reciprocal movement thereof. The lens support 107 includes a stationary portion mounted to upper housing 16 and a movable portion that includes a threaded bore 109. A bolt 108, operably engageable with the bore 109, includes a wheel that is driven by a toothed belt 110 through a corresponding drive wheel 112 of a camera lens focus motor 114 to move the camera lens 100 into focus. The camera lens focus motor 114 is in electrical communication with the electrical components 56 and controlled by a processor included in computer 28.

In addition to automated focus control of the camera lens 100, the system 10 also includes an automated filter select device 117 capable of selectively providing multiple filters 118 at least partially between the camera 20 and the sample. The filters 118 may each facilitate image capture for one or more particular imaging applications. As shown in FIGS. 9 and 11, the optical filter select device 117 includes a circular filter select wheel 116 adapted to carry a plurality of optical filters 118 around its perimeter. The filter select wheel 116 is capable of selectively positioning one of the plurality of optical filters 118 to intersect light emitted from a sample within the cavity interior 44. The wheel 116 is rotatably mounted at its center to a mounting bracket 120 attached to upper housing 16. The filter wheel 116 is mounted off-center from the lens 100 such that the individual filters 118 can each be rotated into position to intersect light emitted from the sample before reaching the camera lens 100. The filter wheel 116 has a groove along its perimeter edge in which a toothed belt 122 is seated. The toothed belt 122 is also engaged with a drive wheel 124 on a filter wheel motor 126. The filter wheel motor 126 is in electrical communication with the electrical components 56 and controlled by a processor included in computer 28. The plurality of optical filters 118 carried by the filter wheel 116 may include any of a variety of optical filters for facilitating image capture such as a neutral density filter for bright samples, one or more wavelength cutoff filters for restricting specific wavelengths, a fluorescent filter for fluorescence applications in which the excitation light differs from the detected light, etc.

In another embodiment, the filter select device 117 comprises a two filter wheel 116 system. In this case, the filter select device 117 includes a first optical filter select wheel 116 and a second optical filter select wheel 116, both of which are rotatably mounted in parallel at their center to the mounting bracket 120 attached to upper housing 16. The first filter select wheel 116 is adapted to position a first set of optical filters included in the plurality of optical filters. The second filter select wheel 116 is adapted to position a second set of optical filters included in the plurality of optical filters. The filter select device 117 may then selectively position a combination of optical filters from the first and second wheels such that light emitted from the sample must pass through two optical filters. In a specific embodiment, the first and second filter select wheels 116 are each adapted to carry seven optical filters. In another specific embodiment, the first and second filter select wheels 116 are each adapted to carry twelve optical filters.

Figure 12:
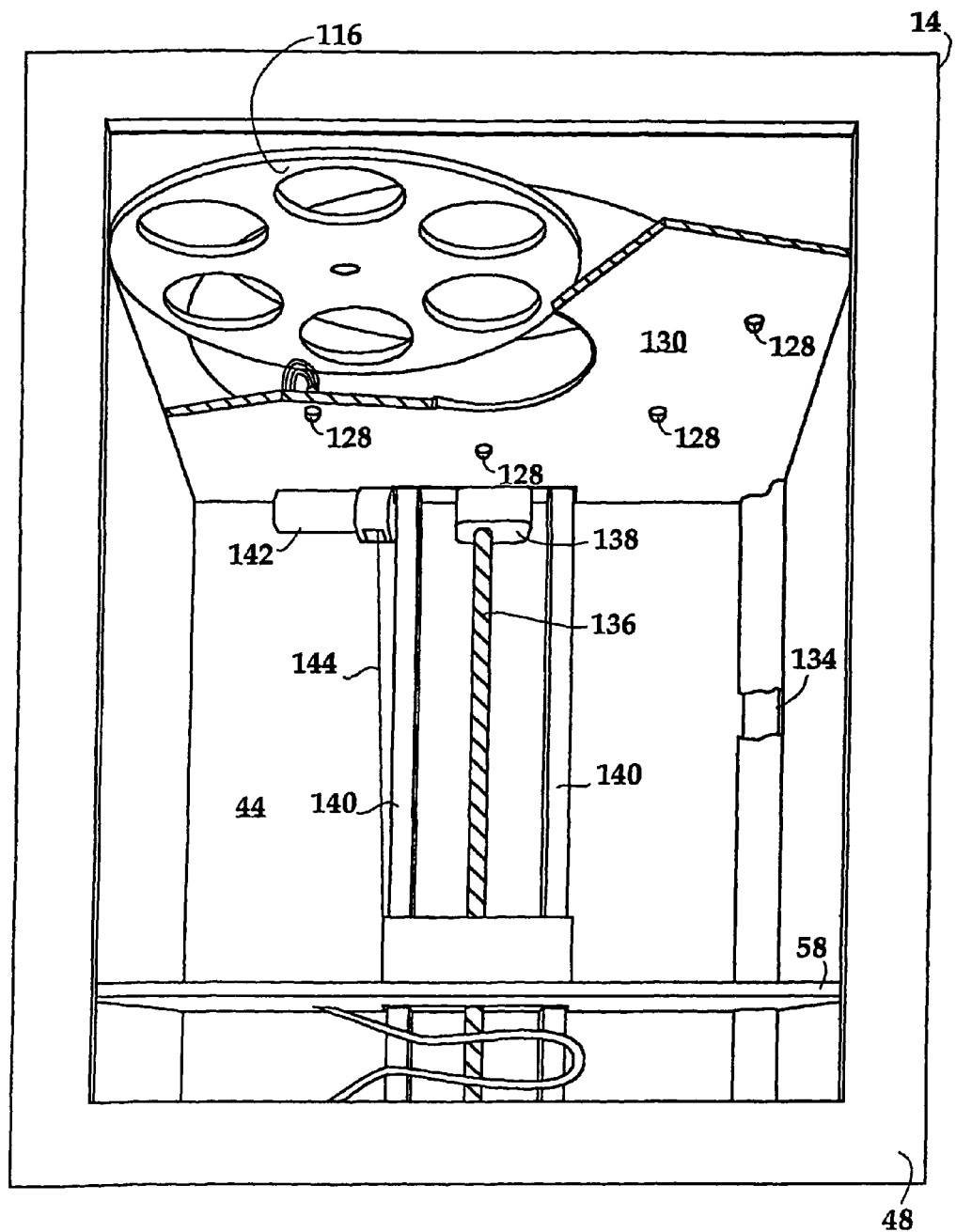
FIG. 12 is a bottom perspective view of the interior of the imaging box of FIG. 2, with portions cut away, showing various features of the box and associated imaging components.

The F-stop motor 106, lens focus motor 114, and filter wheel motor 126 are each stepper motors capable of suitable position control of their respective components. By way of example, a model number SST 39D 1010 (1.8 deg/step, 4.3V, 0.85 A), manufactured by Shinano Kenshi Co., Ltd, Japan, is suitable for use with any of the motors 106, 114 and 126. As shown in FIG. 12, each of the motors 106, 114 and 126 is in electrical communication with one or more electronic components 56 housed in drawer 54 via wires 134. The electronic components 56 are, in turn, in communication with the computer 28 where the motors 106, 114 and 126 may be controlled by appropriate software and/or by user input.

The box 12 also includes a movable stage 58 on which the light-emitting sample is supported. The movable stage 58 is capable of linear, reciprocal movement between the partition 52 and the top enclosure panel 41, and may be retained at any position therebetween for image capture. Thus, the moveable stage 58 has a multiple vertical positions in the interior cavity having the substantially same horizontal position. As shown in FIG. 12, the movable stage 58 has a threaded bore that is operably engaged with a worm gear 136. The worm gear 136 provides vertical translation of the moveable stage 58. A motor 138 (e.g., model number SST 42D 2120 from Shinano Kenshi Co. (1.8 deg/step, 3.7V, 1.2 A)) drives the worm gear 136 to move the stage 58 up and down along a pair of guides 140. In another embodiment, the stage 58 is driven vertically using a belt driven system that provides a faster response than the worm gear 136.

In one embodiment, the movable stage 58 supports a removable vertical wall placed on the upper surface of the movable stage 58. The vertical wall acts as a light shield that prevents light emitting from a sample to translate horizontally across the stage 58 surface to a portion of the moveable stage 58 that does not support the sample. For image capture of multiple samples in which one sample producing excessive light, the vertical wall may then be useful in preventing the excessive light from this sample to undesirably affect imaging of an adjacent sample.

Also associated with the moveable stage 58 is a position sensor 142. The position sensor 142 communicates with the computer 28 and provides a read-out which may be used in position control of the stage 58. In this case, the position sensor 142 includes a string or thin string 144 having one end attached to the moveable stage 58 while the other end is attached to a take-up reel in the position sensor 142. Based on the amount of string 144 wound on the reel and the total length of the string 144, the position sensor 142 is able to determine the length of string between the stage 58 and the sensor 142. This length is then converted into the height of the moveable stage 58 relative to partition 52, e.g., by using a look-up table in computer 28 to carry out the conversion. In another embodiment, the position sensor is a laser positioned in the interior cavity 44 to intercept the moveable stage 58 at a starting vertical position. The laser may then be used to calibrate the position of the moveable stage 58 to the starting vertical position.

In many imaging applications, the low intensity light source may be embodied in any of a variety of light-emitting animals containing light-emitting molecules, such as various mammalian subjects containing luciferase expressing cells. Often, thermoregulatory functioning of the animal has been compromised to facilitate analysis or image capture, e.g. many laboratory mice are genetically hairless or the mice are sedated during imaging to minimize any movement that may compromise imaging. Correspondingly, in one embodiment of the present invention, the system 10 includes a temperature control element 132, e.g., a heater or cooler, configured to control the temperature of one of the sample and the interior cavity 44, or both. For example, while imaging mammals or mammalian cells, it is often desirable to maintain the specimens at or near 37 degrees Celsius. In these cases, the imaging system 10 keeps the stage 58 and sample warm by heat provided by the temperature control element 132 at or near 37 degrees Celsius.

In the embodiment shown in FIG. 11, the temperature control element 132 is provided by a heating blanket placed on top of stage 58. In another embodiment, as shown in FIGS.

12 and 13A, the temperature-adjusting element 132 is a thermal sheet 160 for controlling the temperature of the sample (such as M2436 1234 24V 35W as provided by Instrument Labs of Los Angeles, Calif.) that is fixed, e.g. glued. into a cut-away portion of stage 58. The temperature-adjusting element 132 includes heating element lead 162 which supplies the power for heating element 160 and extends from thermal sheet 160 and is in electrical communication with electronic components 56 housed in drawer 54. Together, the heating element lead 162, electronic components 56 and computer 28 allow temperature and heat control of the temperature-adjusting element 132.

As mentioned before, it is often desirable to sedate a light-emitting animal during imaging to minimize any movement that may affect imaging. In many cases, an anesthetizing gas is supplied to the animal to keep the animal sedated for an extended period of time. In these cases, the imaging system 10 includes a gas delivery system 220 detachably mounted on the moveable stage 58 to deliver a gas to the sample.

Figure 13:
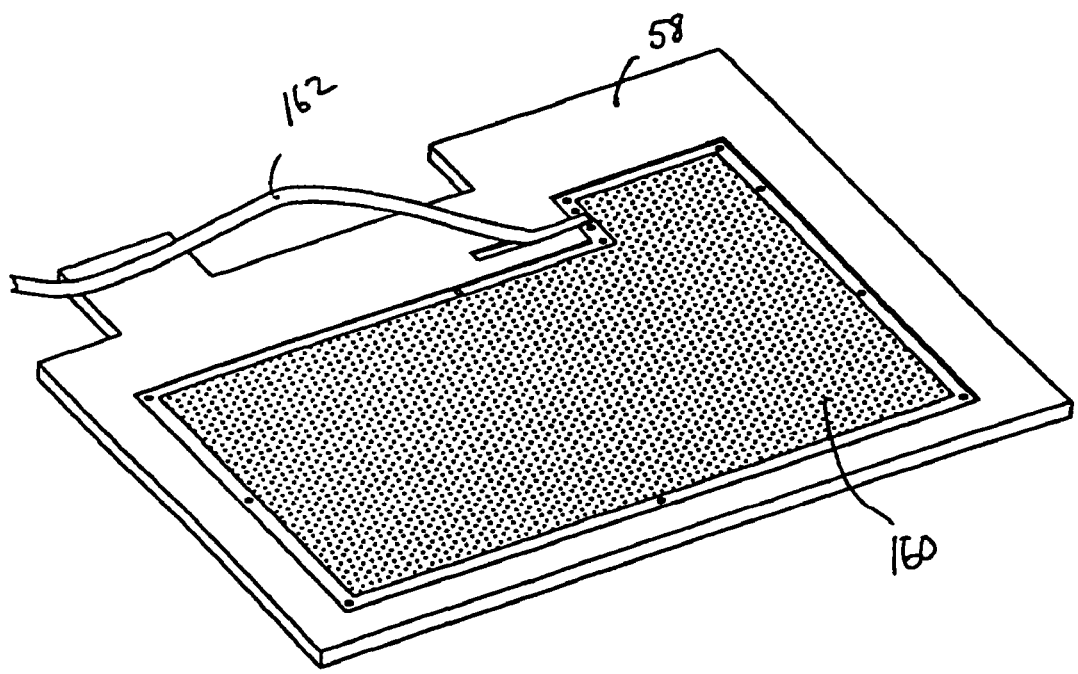
FIG. 13A is a perspective view of the moveable stage of the imaging box of FIG. 2 showing an integrated heating element in accordance with one embodiment of the present invention.
FIGS. 13B-C are side and top views, respectively, of a gas delivery system comprising a gas manifold detachably coupled to the moveable stage of the imaging box of FIG. 2 in in accordance with one embodiment of the present invention.
Figure 13B:
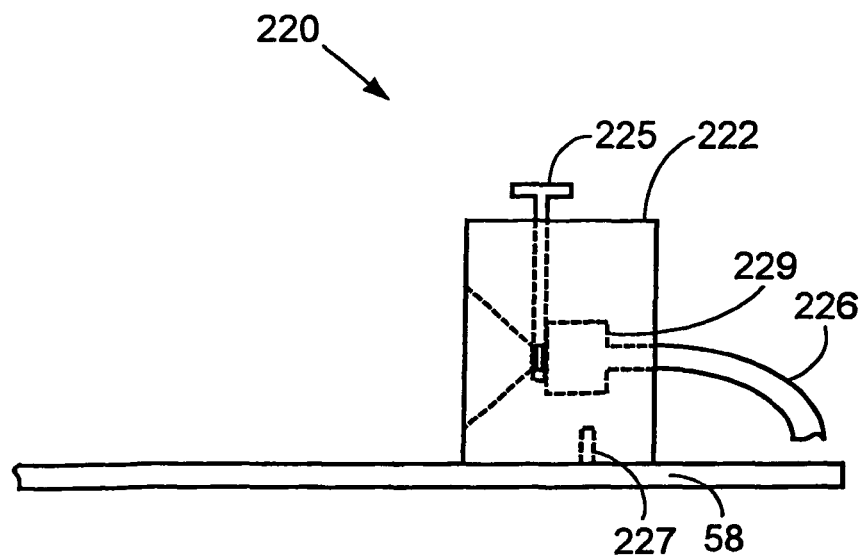
Figure 13C:
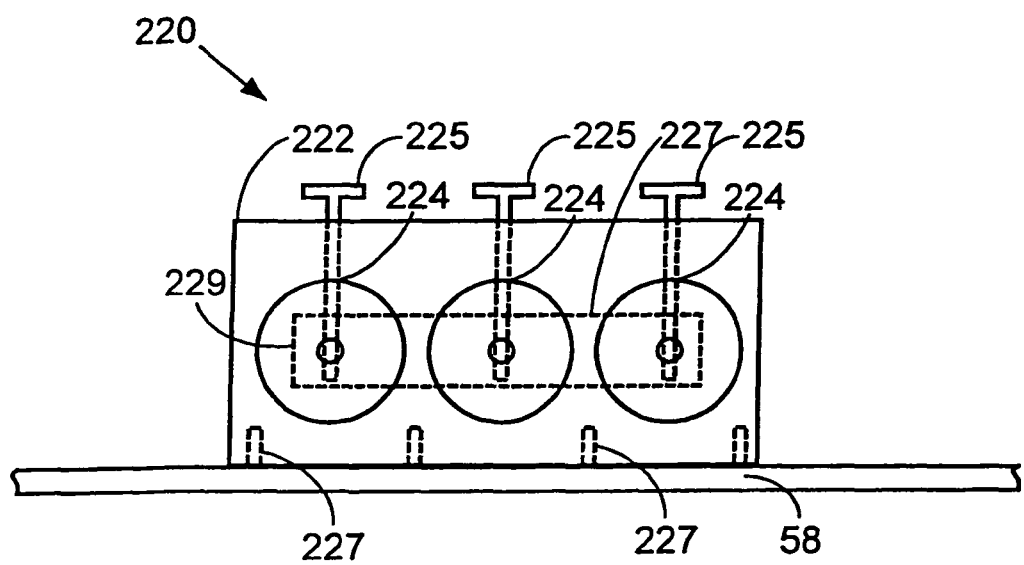

In the embodiment shown in FIGS. 13B-C, the gas delivery system 220 comprises a gas manifold 222 detachably coupled to the moveable stage 58. The gas manifold 222 includes a plurality of interfaces 224. Each interface 224 is adapted to provide a gas to a sample resting on the moveable stage 58. In a specific embodiment, the gas manifold 222 comprises five interfaces 224 that are each funnel shaped to accommodate different sized samples. The gas manifold 222 may be screwed using bolts 227 or otherwise fixed to the stage 58 in a detachable manner. A valve 225 associated with each interface 224 controls gas flow to the sample through its respective interface. A tube 226 supplies gas to the gas manifold 222 and extends from outside the box 12. To reach a sample, gas supplied from the tube 226 flows through a channel 229 to an interface 224 that accommodates the sample. In one embodiment, the tube 226 includes a distal end that is open to the environment outside the box 12. In this case, the tube 226 is substantially long and extends along a large distance in the cavity interior 44 with numerous turns. The tube 226 also has a large length to cross sectional area and includes non-reflective surfaces that minimize light passage through the tube 226. As a result, the end of the tube 226 inside the cavity interior 44 emits substantially no light within the cavity interior 44. In a specific embodiment, the tube 226 has a diameter of ¼" ID to ⅜" OD inches and a length of about 85 to about 90 inches and is made of black PVC. A second tube 228 may also be included as a gas outlet.

As light retained in any elements inside the box 12 may undesirably affect subsequent luminescent image capture, the manifold 222 comprises a non-reflective surface and a non-light retaining material. In a specific embodiment, the gas manifold 222 is made of glass that does not retain light introduced to the manifold 222 when the door 18 is open. In another embodiment, the gas manifold 222 is autoclavable. The autoclavable gas manifold 222 allows simple sterilization and contaminants to easily be removed from the gas manifold 222. For example, the gas manifold 222 may be autoclaved by subjecting the manifold 222 to high temperatures and pressures, e.g., up to about 60 psi and about 130 degrees Celsius. Together, the tube 226, gas manifold 222, and interfaces 224 gas supply to one or more samples in the cavity interior 44 from a gas source outside the box 12. A knob may also be included on an outside surface of the box 12 to control gas supply through the tube 226.

Figure 14A:
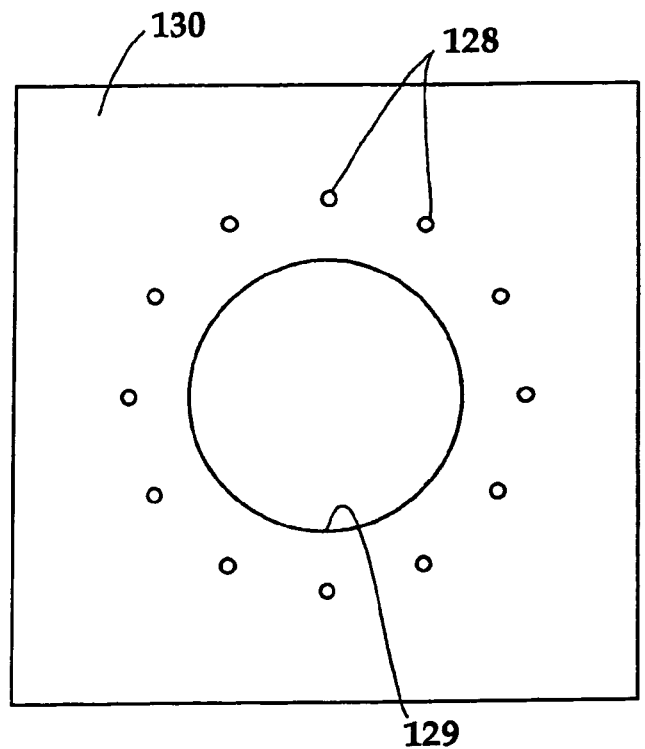
FIG. 14A is a top view of a light source mounted in the imaging box of FIG. 2 according to one embodiment of the invention.
Figure 14B:
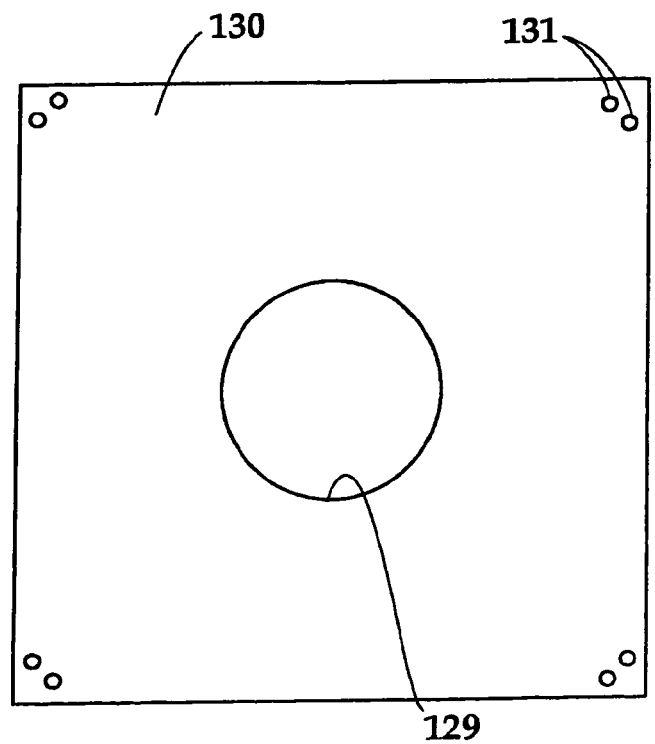
FIG. 14B is a top view of a light source mounted in the imaging box of FIG. 2 according to another embodiment of the invention.

In accordance with another aspect of the present invention, a light source is provided in the interior cavity 44 for illuminating the sample or specimen in the imaging box 12. The light source may be continuously illuminated or flashed while capturing photographic images of the sample and is turned off for capturing luminescence images. As illustrated in FIG. 14A, the light source comprises a ring of low-wattage lights 128 mounted on the bottom surface of a partition 130 positioned around the camera lens 100. The partition 130 is positioned below the other components housed in the top area of the box and separates the upper portion of the box 12 from the cavity 44. The partition 130 is attached to at least one side of the box 12 and also includes a hole 129 for camera 100 visibility. In another embodiment, as illustrated in FIG. 14B, the light source comprises four pairs of white-light emitting diodes (LEDs) 131, one pair mounted in each of the corners of partition 130 around the camera lens 100. One advantage of using such LEDs is that the spectral emission thereof may be contained to visible light while excluding infrared light. Wires (not shown) may extend from the light low-wattage lights 128 to the electronic components 56 and computer 28 to allow light levels to be controlled externally through the computer 28.

The light source may also include a fiber optic cable. In a specific embodiment, the fiber optic cable has a first end located in the interior cavity 44 and a second end located outside the box 12. The first end may be used to illuminate the sample while the second end extends outside the box 12 to a light source that provides the light to the optic cable. Within the cavity interior 44, the fiber optic cable may be contained in a flexible "snake-like" housing that maintains a desired position of the first end as provided by a user. This allows the user to flexibly position the first end relatively close to the sample for illumination in a particular photographic capture. A filter may also be used with the fiber optic light source to provide a particular lighting effect. In a specific embodiment, the fiber optic light source is used to make various samples fluoresce and the filter is used to select the wavelength of light to excite the sample. In this case, filters in the filter select device 117 of FIG. 9 allow a camera to only receive selected light that is fluorescing in the sample. When the second end is located outside the box 12, the imaging box 12 includes a hole that allows said fiber optic cable to pass therethrough. When the optic cable is not in use, the hole may be suitably plugged to prevent light from entering the box. In another embodiment, there is a break in the fiber optic cable at the box 12 wall that allows a user to remove either the outside or inside fiber and cap the remaining end off to minimize light leakage to the inside of the box 12.

To provide additional light protection for the interior cavity 44, one or more walls forming the cavity 44 may be light sealed. For example, it may be advantageous to light seal the partition 52 and/or the top enclosure panel 41 (FIG. 11).

Figure 1D:
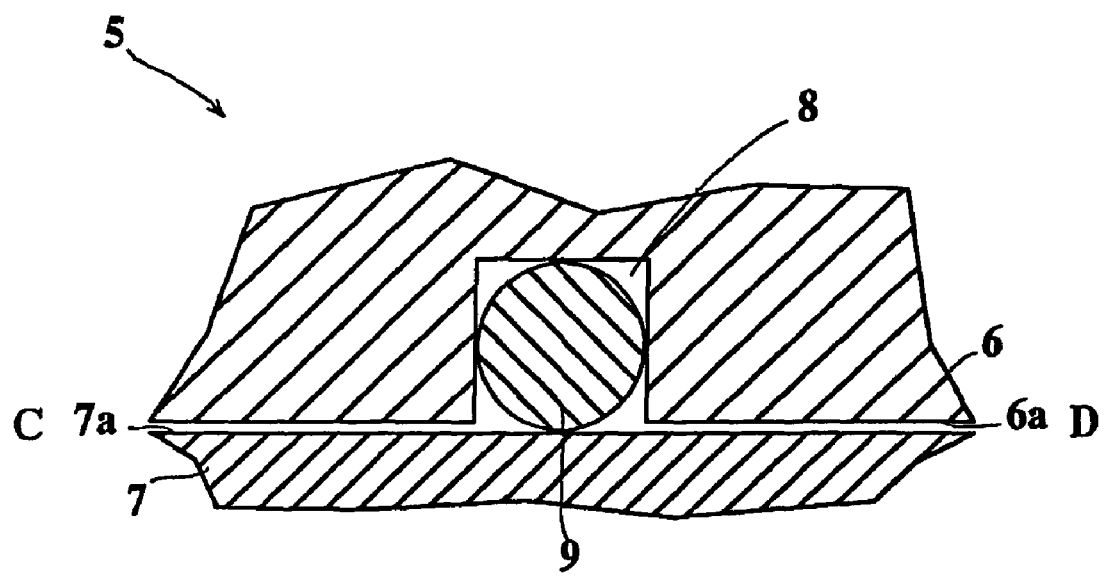
FIG. 1D is an enlarged, cross-sectional view of a conventional seal between two surfaces.

FIG. 1D is a cross-sectional view of a conventional seal 5 that may be used for preventing light from entering an enclosure between two adjacent walls 6 and 7 of the enclosure housing. The seal 5 is formed between two opposed surfaces 6a and 7a of the walls 6 and 7 to be joined. Together, the opposed surfaces 6 and 7 form a channel 8 for receipt of an o-ring 9. Only one of the surfaces, surface 6a, is recessed for the channel 8, while the other surface 7a is flat.

Figure 15:
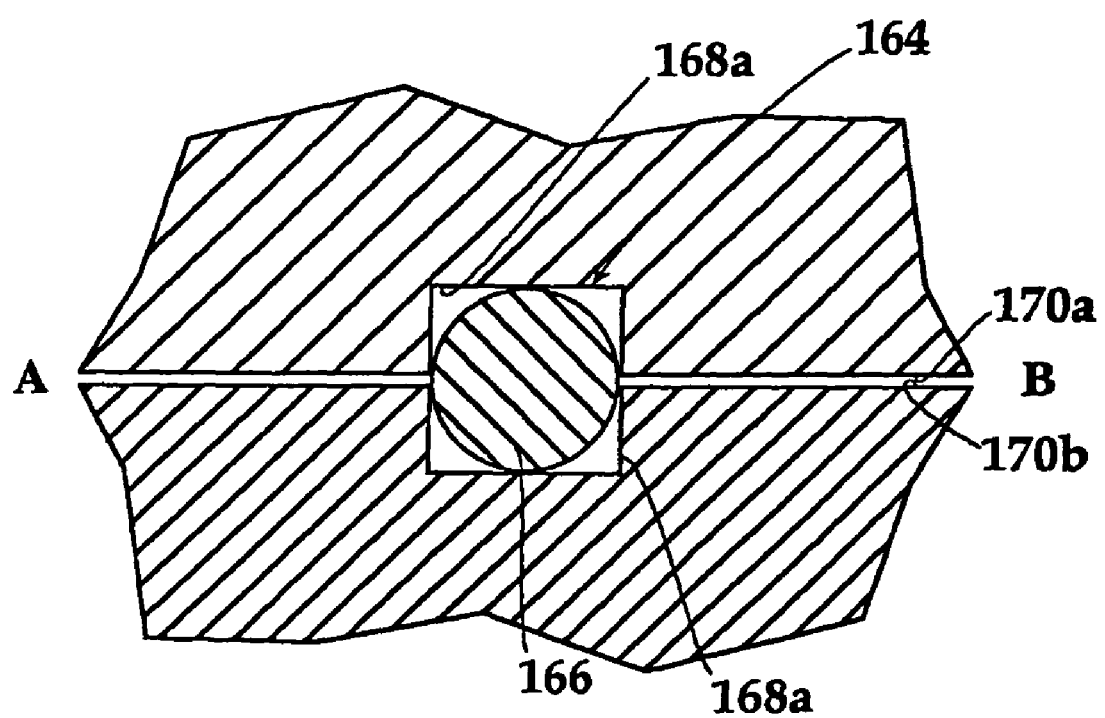
FIG. 15 is a cross-sectional view of an "o-ring" light-seal according to another embodiment of the invention.

FIG. 15 shows a light seal 164 in accordance with one embodiment of the present invention. Light seal 164 is employed, for example, in the assembly of upper housing 16, and at the contact between upper housing 16 and top plate 103 (see FIG. 11 for both cases) and is used for preventing light from entering the cavity 44 from the top portion of the box 12. Light seal 164 includes a gasket 166 which is composed of compressible material, such as a rubber o-ring, and two opposing channels 168a and 168b, each located in one of two substantially planar surfaces 170a and 170b. The surface 170a, defining the first channel 168a, and the second surface 170b, defining the second channel 168b, are configured such that the channels are aligned at least partially with each other. The compressible gasket 166 is disposed in the channels 168a and 168b and configured to contact opposing edges of the channels 168a and 168b when the surfaces 170a and 170b are positioned in opposed relationship to one another. In addition, the gasket 166 and channels 168a and 168b may also be configured such that the gasket 166 is positioned at the intersecting edges between the channels 168a and 168b and the corresponding surfaces 170a and 170b.

In accordance with this aspect of the present invention, this light seal 164 is a more effective light barrier than the conventional seal 5 of FIG. 1D. In the conventional seal, if there is a slight gap between the seal 9 and the surface 7a such as an inconsistency in either of the surfaces 6a and 7a along the o-ring 9 length, light can pass between points C and D with virtually no change in direction. In contrast, when there is an imperfection in the sealing of the o-ring 166 against one of the flat surfaces in FIG. 15, entering light would require multiple direction changes to pass between points A and B. Accordingly, the light seal 164 reduces the amount of light entering the cavity 44 due to any defects in the light seal 164 along its length.

Figure 16:
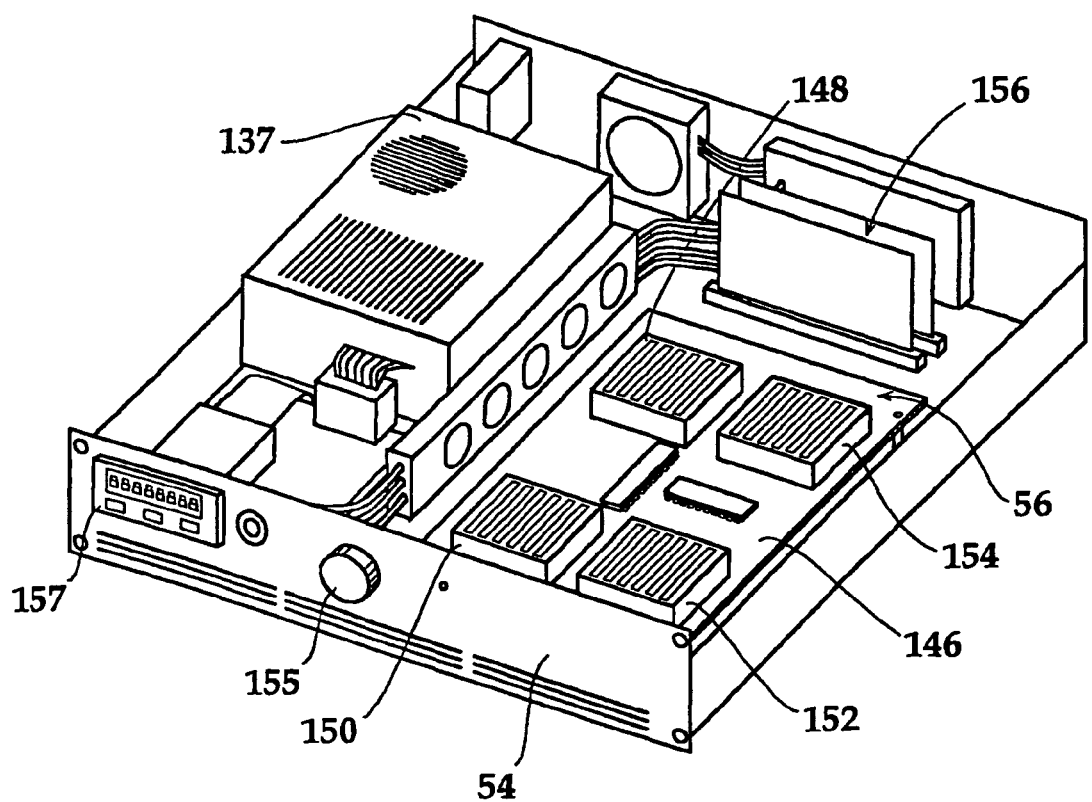
FIG. 16 is a perspective view of the electronic component drawer of the imaging box of FIG. 2 in accordance with one embodiment of the present invention.

Referring now to FIG. 16, there is shown a top perspective view of drawer 54 and electronic components 56 housed therein. As previously noted, these components interface with the computer 28 and are used to control the various motors and other components of the imaging system 10. A 3 V power supply 137 provides electrical power to the various active components in the drawer 54. A motor control board 146 has four motor controllers 148, 150, 152, 154 mounted thereon. The motor controllers 148, 150, 152, 154 are in communication with each of the F-stop motor 106, lens focus motor 114, and filter wheel motor 126 and stage motor 138, respectively, via wires 134. Each motor controller interfaces, via cable 34, with the computer 28 where the motor controllers and motors may be controlled by appropriate software running on the computer and user input. Drawer 54 also houses a data acquisition board (DAB) 156. On the face of the drawer is a knob 155 which is in communication with light source 128 and allows the user to manually to control the light intensity in the interior cavity 44. Also on the drawer face is a heater controller 158 which is in communication with heating element lead 162 to control and display its temperature.

B. Comparison of the Imaging System of the Present Invention with a Conventional Light Box Tests were conducted to compare a conventional light box—model number A4178 as manufactured by Hamamatsu Photonic Systems of Bellerica, Mass.—and an imaging box in accordance with one embodiment of the present invention. Each box was tested under substantially identical conditions. For the Hamamatsu box, a camera was installed on and operably connected with image capturing equipment. A piece of white paper was placed inside the box, approximately 12" away from the front of the camera lens, to serve as a reflective sample. The door of the box was closed, and an image was acquired with the exterior room lights on. The room lights were then turned off, and a second image was acquired. The total amount of light acquired under the two conditions was compared. The camera was then transferred to an imaging box of the present invention, and images were acquired under the same conditions.

The testing showed that approximately 130% to 140% more external light entered the Hamamatsu box with the exterior lights on than with them off. In comparison, the imaging box of the present invention measured only about a 3% increase in the amount of light entering the box with the exterior lights on as compared with the exterior lights off.

II. Operation of the Imaging System of the Present Invention

The present invention may be employed in a wide variety of imaging applications. Generally, the present invention may be applied with any non-invasive methods and compositions for detecting, localizing and tracking light-emitting entities and biological events in a mammalian subject. For example, the imaging system 10 may be implemented with intensified Charge-Coupled Device (CCD) cameras to detect the localization of light-producing cells (e.g., certain bacteria or tumor cells made bioluminescent by transforming them with luciferase DNA constructs) inside of living animals, such as mice. In such applications, an animal containing the bioluminescent cells is placed inside of the specimen chamber, and within the field of a photodetection device, such as an intensified CCD camera. The camera is then activated to detect the emitted photons. The photon signal may then be used to construct a luminescent image of photon emission. The luminescent image is constructed without using light sources other than the luminescence from the sample itself. This luminescence is recorded as a function of position to produce the luminescence image. The photographic image may also be taken of the same sample to aid in position visualization of the luminescent image. One approach to generating such composite photographic/luminescence images is described in U.S. Pat. No. 5,650,135 issued to Contag et al. on Jul. 22, 1997. The entire disclosure of that patent is incorporated herein by reference for all purposes.

Figure 17:
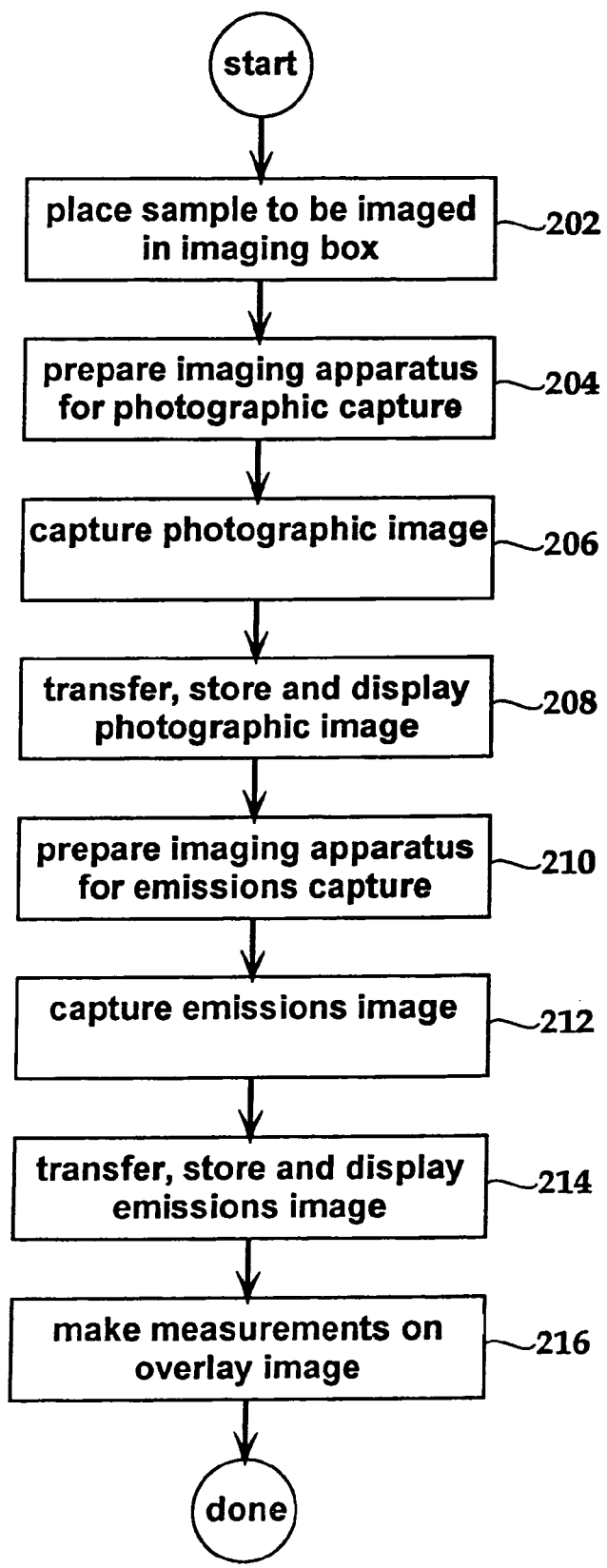
FIG. 17 is a flow chart illustrating a method of capturing photographic and luminescence images using the imaging box of FIG. 2 in accordance with embodiments of the invention.

Turning now to FIG. 17, a flow chart illustrates a method of capturing photographic and luminescent images using the imaging system 10 in accordance with of the invention. The method begins by placing a sample or specimen to be assayed for light emission on the stage in the imaging box 12 (202). The imaging box 12 and associated image components are then prepared for capturing a photographic image of the sample (204). The preparation may include launching imaging and acquisition software (e.g., "LivingImage", Xenogen Corporation, Alameda, Calif.) on the computer 28 and initializing the camera 20. Further preparations may include selecting the desired stage 58 position, closing the door 12, activating the photographic capture option in the software, and turning on the lights (e.g., lights 128 or 132) in the box. Preparations may further include focusing the lens 100, selectively positioning an appropriate lens filter 118, setting the f-stop, etc.

The photographic image is then captured (206). In one embodiment, a "live mode" is used during photographic imaging of the sample to observe the sample in real time. The live mode includes a sequence of photographic images taken frequently enough to simulate live video. Upon completion of photographic capture, the photographic image data are transferred to an image processing unit 26 and/or computer system 28 (208). These may be used to manipulate and store the photographic image data as well as process the data for display on computer monitor 38.

Subsequently, imaging box 12 and associated image components are prepared for luminescence image capture (210). Such preparation may include, for example, selecting luminescent exposure time and binning level using the computer 28, and turning off the lights in the cavity 44. The CCD camera 20 then captures (212) the luminescence image over a set period of time (up to several minutes). The luminescence image data are transferred to the image processing unit 26 and/or computer 28 (214), which may be used to manipulate and store the luminescence image data as well as process it for display on the computer display 38 (step 214). The manipulation may also include overlaying the luminescent image with the photographic image and displaying the two images together as an "overlay" image, with the luminescence data typically shown in pseudocolor to show intensity. This overlay image may then be the basis for user analysis (216). At this point, the user has the components of a digital overlay image (including the luminescence image and the photographic image) stored in the computer 28. The information contained in these image may be analyzed and manipulated as desired.

Based on the foregoing, it should be readily apparent to those skilled in the art that a substantially improved imaging box for imaging low intensity light sources has been disclosed. The improved sealing arrangements and door securing designs of the present invention provide substantially more light-tight enclosures than have been previously available. Various additional improved features of an imaging box have also been disclosed, including a novel automated filter select device, automated camera focusing, f-stop adjustment, automated stage height, internal illumination and sample temperature control. Moreover, it will be apparent to those skilled in the art in light of the foregoing disclosure that further alternatives, modifications and variations are possible. For example, imaging systems in accordance with the present invention may not necessarily include all the improvements and embodiment disclosed herein and may include any one or more of the above described embodiments. In addition, the present invention is suitable for other imaging applications and may be tailored correspondingly. By way of example, the present invention may be adapted for analysis of high detail in-vivo applications and thus may include zoom tools for the camera 20 and controlling computer 28. Also, the various properties and characteristics of the compressible material 62 are by way of example only and other materials and variations may be suitable. Although various details have been omitted for brevity's sake, obvious design alternatives may be implemented. Therefore, the present examples are to be considered as illustrative and not restrictive, and the invention is not to be limited to the details given herein, but may be modified within the scope of the appended claims.

What is claimed is:

1. A light-tight imaging system for capturing an image of a sample, the imaging system comprising:
    an imaging box including:
        a body including an interior cavity for receiving the sample, and having a front portion defining an opening into said cavity, said body further including a view hole enabling viewing of the sample; and
        a door having a rear portion, said door movable between an opened condition, enabling access to the interior cavity through the cavity opening, and a closed condition, positioning said rear portion substantially adjacent the body front portion to prevent access through the cavity opening;
    a moveable stage disposed in the cavity interior that supports the sample, said moveable stage being adapted to selectively position the sample at a selected one of a plurality of vertical positions relative to the view hole, wherein each of the plurality of vertical positions has substantially the same horizontal position in the interior cavity and each is substantially linearly closer to or substantially linearly further away from said view hole with respect to every other vertical position; and
    a light shield supported by said moveable stage, said light shield preventing light from said sample to translate horizontally to a portion of the moveable stage that does not support said sample, wherein said light shield includes a substantially vertical wall upstanding from a surface of the moveable stage.

2. The imaging system according to claim 1, further including:
    a temperature control element configured to alter the temperature of one of the sample and the interior cavity.

3. The imaging system according to claim 2, wherein the temperature control element includes a thermal sheet in thermal communication with said moveable stage.

4. The imaging system according to claim 1, further including:
    a gas manifold device in communication with said interior cavity, and configured to supply a gas to the sample, wherein said gas manifold device is coupled to said moveable stage.

5. The imaging system according to claim 1, further including:
    a positioning sensor, wherein said positioning sensor cooperates with the moveable stage to determine its position relative to said view port.

6. The imaging system according to claim 5, wherein said positioning sensor includes a laser positioned in said interior cavity to intercept said moveable stage at the selected one of a plurality of positions relative to the view hole at said first vertical position.

7. The imaging system according to claim 1, further including:
    a drive assembly coupled to the moveable stage to selectively move said moveable stage to the selected one of a plurality of positions.

8. The imaging system according to claim 1, further including:
    a partition located in the cavity interior, the partition forming a compartment within the body separate from the interior cavity.

9. An imaging system for capturing an image of a sample, the imaging system comprising:
    an imaging box having:
        a body including an interior cavity for receiving the sample, and having a front wall defining an opening into said cavity;
        a door having a rear wall and an exterior face, said door movable between an opened condition, enabling access to the interior cavity through the cavity opening, and a closed condition, positioning said rear wall substantially adjacent the body front wall to prevent access through the cavity opening;
    a moveable stage in the cavity interior that supports the sample, the moveable stage having a first vertical position and a second vertical position in the interior cavity, wherein the first vertical position and the second vertical position have the substantially same horizontal position in the interior cavity, and
    a light shield supported by said moveable stage, said light shield preventing light from said sample to translate horizontally to a portion of the moveable stage that does not support said sample, wherein said light shield includes a substantially vertical wall upstanding from a surface of the moveable stage.

10. The imaging system of claim 9 further including:
    a temperature control element configured to alter the temperature of one of the sample or the interior cavity, wherein the temperature control element is a thermal sheet in thermal communication with said moveable stage.

11. The imaging system of claim 9, further including:

a gas manifold coupled to said moveable stage, the gas manifold configured to supply a gas to the sample.

12. The imaging system of claim 9, further including:

a laser positioned in said interior cavity to intercept said moveable stage at said first vertical position.

13. The imaging system of claim 9, further including:

a worm gear coupled to the moveable stage that provides vertical translation of the moveable stage between the first vertical position and the second vertical position.

14. The imaging system of claim 9, further including:

a partition located in the cavity interior, the partition forming a compartment within the body separate from the interior cavity.

15. The imaging system of claim 14, wherein the compartment includes an opening formed in the body and the compartment is adapted to slideably receive a drawer through the opening.

16. The imaging system of claim 15, wherein the drawer houses electronics equipment used to control components within the imaging box.

* * * * *